(12) United States Patent
Braslawsky et al.

(10) Patent No.: US 6,897,044 B1
(45) Date of Patent: May 24, 2005

(54) PRODUCTION OF TETRAVALENT ANTIBODIES

(75) Inventors: Gary R Braslawsky, San Diego, CA (US); Nabil Hanna, Rancho Santa Fe, CA (US); Kandasamy Hariharan, San Diego, CA (US); Michael J LaBarre, San Diego, CA (US); Tri B Huynh, San Diego, CA (US)

(73) Assignee: Biogen Idec, Inc., San Diego, CA (US)

( * ) Notice: Subject to any disclaimer, the term of this patent is extended or adjusted under 35 U.S.C. 154(b) by 0 days.

(21) Appl. No.: 09/238,741

(22) Filed: Jan. 28, 1999

(51) Int. Cl.[7] .............................................. C12N 15/00
(52) U.S. Cl. ............... 435/69.6; 530/387.3; 530/388.85
(58) Field of Search .......................... 530/387.1, 387.3, 530/383.8, 388.85; 435/69.2, 69.6; 536/23.1, 23.53

(56) References Cited

U.S. PATENT DOCUMENTS 5,830,698 A    11/1998  Reff
6,011,138 A  *  1/2000  Reff et al.

FOREIGN PATENT DOCUMENTS

WO    WO 91 19515    12/1991
WO    WO 96/14339     5/1996
WO    WO 99/66951    12/1999

OTHER PUBLICATIONS

Cruse et al., Illustrated Dictionary of Immunology. CRC Press. p. 19, 1995.*
The Pierce Catalog, pp. T–157, T163–T169, 1994–1995.*
Brenner et al. Science 229 81–883, 1985.*
Reff et al Blood 83 435–445, 1994.*
Fanger et al. Critical Reviews in Immunology 12 101–124, 1992.*
Paul. Fundamental Immunology, Raven Press, NY chapter 8, p. 242, 1993.*
Panka et al PNAS 85 3080–3084, 1988.*
Demidem A, et al., "Chimeric anti–CD20 (IDEC–C2B8) monoclonal antibody sensitizes a B cell lymphoma cell line to cell killing by cytotoxic drugs," *Cancer Biotherapy & Radiopharmaceuticals*, 1997, 12(3):177–186.
Featherstone, "Bispecific antibodies: the new magic bullets, "*Lancet*, 1996, 348:536.
Ghetie M, et al., "Homodimerization of tumor–reactive monoclonal antibodies markedly Increases their ablility to induce growth arrest or apoptosis of tumor cells," *Proc. Natl. Acad. Sci. USA*, 1997, 94: 7509–7514.
Hartmann, et al., "Treatment of Hodgkin's disease with bispecific antibodies," *Annals of Oncology 7 (Suppl 4)*, 1996, S143–S146.
Kroesen, et al., "The role of apoptosis: a bispecific antibody–mediated T–cell cytotoxicity", *Br. J. Cancer*, 1996, 73(6): 721–727.

Ring, et al., "Antigen forks: bispecific reagents that Inhibit cell growth by binding selected pairs of tumor antigens," *Cancer Immunology Immunotherapy*, 1994, 39: 41–48.
Shan et al., "Apoptosis of malignant human B cells by ligation of CD20 with monoclonal antibodies," *Blood*, 1998, 91(5): 1644–1652.
Shopes, "A genetically engineered huam IgG mutant with enhanced cytolytic activity," *J. Immun.*, 1992, 148(9): 2918–2922.
Snider et al., "Processing fate of protein antigen attached to IgD or MHC molecules on normal B lymphocytes using heterocrosslinked bispecific antibodies," *Molecular Immun.*, 1991, 28(7):779–788.
Brennan M, et al., "Preparation of bispecific antibodies by chemical recombination of monoclonal immunoglobulin G1 fragments," *Science*, 1985, 229:81–3.
Chaouchi N, et al., "B cell antigen receptor–mediated apoptosis, Importance of accessory molecules CD19 and CD22, and of surface IgM cross–linking," *J. Immunol*, 1995, 154:3096–104.
Clark EA, et al., "Role of the Bp35 cell surface polypeptide in human B–cell activation," *Proc Natl Acad Sci U S A*, 1985, 82:1766–70.
Clark EA, et al., "Structure, function, and genetics of human B cell–associated surface molecules," *Adv Cancer Res*, 1989, 52: 81–149.
FitzGerald K, et al., "Improved tumour targeting by disulphide stabilized diabodies expressed in *Pichia pastoris*," *Protein Eng*, 1997, 10: 1221–5.
Funakoshi S, et al., "Differential in vitro and in vivo antitumor effects mediated by anti–CD40 and anti–CD20 monoclonal antibodies against human B–cell lymphomas," *J. Immunother Emphasis Tumor Immunol*, 1996, 19:93–101.
Hoider M, et al., "Engagement of CD20 suppresses apoptosis in germinal center B cells," *Eur. J. Immunol.*, 1995, 25:3160–64.
Hooijberg E, et al., "Enhanced antitumor effects of CD20 over CD19 monoclonal antibodies in a nude mouse xenograft model," *Cancer.Res.*, 1995, 55:840–6.

(Continued)

*Primary Examiner*—Larry R. Helms
(74) *Attorney, Agent, or Firm*—Pillsbury Winthrop LLP

(57) ABSTRACT

The present invention relates to a novel process for the preparation of biologically active antibody dimers in a pharmaceutically acceptable composition. The dimers can be composed of two antibody molecules having the same antigen binding specificity and linked through reducible, disulfide, or a non-reducible thioether, bond (homodimer). Alternatively, the dimers can be composed of two different antibody molecules having binding specificity for two distinct antigens (heterodimer). These dimers are useful for inducing hyper-cross-linking of membrane antigens. The present invention further relates to the use of biologically active antibody dimers for the preferential killing or inhibition of selected cell populations in the treatment of diseases such as cancer and autoimmune disorders.

32 Claims, 20 Drawing Sheets

OTHER PUBLICATIONS

Jiang Liying et al., "Enhanced effector functions of dimeric forms of IDEC–C2B8 (rituximab)," *Blood*, 1999, 94(10):86a (Astract No. 376).

Maloney DG, et al., "Phase I clinical trial using escalating single–dose infusion of chimeric anti–CD20 monoclonal antibody (IDEC–C2B8) in patients with recurrent B–cell lymphoma," *Blood*, 1994, 84:2457–66.

Maloney et al., "IDEC–C2B8: results of a phase I multiple–dose trial in patients with relapsed non–Hodgkin's lymphoma," *J Clin Oncol*, 1997, 15(10):3266.

McLaughlin et al., "IDEC–C2B (rituximab): clinical activity in clinically chemoresistant (CCRD) low–grade of follicular lymphome (LG/F NHL) and in patients (pts) relapsing after anthracycline therapy (ANTRA–RX) of ABMT," *Proc. Am. Soc. Clin. Oncol.*, 1997, 16: 16a (Abstract 55).

McLaughlin et al., "Rituximab Chimeric Anti–CD20 Monoclonal Antibody Therapy for Replased Indolent Lymphome: Half of Patients Respond to a Four–Dose Treatment Program," J Clin Oncol., 1998, 16(8):2825–33.

Merchant AM et al., "An efficient route to human bispecific IgG," *Nature Biotechnology*, 1998, 16(7):1087 (Abstract).

Newell MK, et al., "Ligation of major histocompatibility complex class II molecules mediated apoptotic cell death in resting B lymphocytes," *Proc Natl Acad Sci USA*, 1993, 90: 10459–63.

Press OW, et al., "Monoclonal antibody 1F5 (anit–CD20) serotherapy of human B cell lymphomas," *Blood*, 1987, 69: 584–91.

Siegall CB, et al., "Cytotoxicity of chimeric (human–murine) monoclonal antibody BR96 IgG, F(ab')2, and Fab' conjugated to *Pseudomonas exotoxin*," *Bioconjug Chem*, 1992, 3:302–7.

Tedder TF, et al., "Antibodies reactive with the B1 molecule inhibit cell cycle progression but not activation of human B lymphocytes," *Eur J Immunol*, 1986, 16:881–7.

Tedder TF, et al., "CD20: a regulator of cell–cycle progression of B lymphocytes," *Immunol Today*, 1994, 15:450–4.

Valentine MA, et al., "Rescue from anti–IgM–induced programmed cell death by the B cell surface proteins CD20 and CD40," *Eur J Immunol*, 1992, 22: 3141–8.

Varadarajan et al., "Conjugation of Phenyl Isothiocyanate Derivatives of Carborane to Antitumor Antibody and In Vivo Localization of Conjugates in Nude Mice," *Bioconj. Chem.*, 1991, 2: 102–110.

Willner D, et al., "(6–Maleimidocaproyl)hydrazone of doxorubicin—a new derivative for the preparation of immunoconjugates of doxorubicin," *Bioconjug Chem*, 1993, 4: 521–7.

Wolff EA, et al., "Monoclonal antibody homodimers: enhanced antitumor activity in nude mice," *Cancer Res*, 1993, 53:2560–5.

\* cited by examiner

Figure 1A

DNA and Predicted Amino Acid Sequences
of the "Dimeric" Anti-CD20 Light Chain (Version 1)

```
     Start           [Murine Natural Leader]
     ATG GAT TTT CAG GTG CAG ATT ATC AGC TTC CTG CTA ATC AGT GCT TCA GTC ATA
     --- --- --- --- --- --- --- --- --- --- --- --- --- --- --- --- --- ---
     Met Asp Phe Gln Val Gln Ile Ile Ser Phe Leu Leu Ile Ser Ala Ser Val Ile ATG TCC AGA GGA|CAA ATT GTT CTC TCC CAG TCT CCA GCA ATC CTG TCT GCA TCT
     --- --- --- ---|--- --- --- --- --- --- --- --- --- --- --- --- --- ---
     Met Ser Arg Gly|Gln Ile Val Leu Ser Gln Ser Pro Ala Ile Leu Ser Ala Ser CCA GGG GAG AAG GTC ACA ATG ACT TGC AGG GCC AGC TCA AGT GTA AGT TAC ATC
     --- --- --- --- --- --- --- --- --- --- --- --- --- --- --- --- --- ---
  15 Pro Gly Glu Lys Val Thr Met Thr Cys Arg Ala Ser Ser Ser Val Ser Tyr Ile
                   [Murine Anti-Human CD20 Light Chain Variable]
     CAC TGG TTC CAG CAG AAG CCA GGA TCC TCC CCC AAA CGC TGG ATT TAT GCC ACA
     --- --- --- --- --- --- --- --- --- --- --- --- --- --- --- --- --- ---
  33 His Trp Phe Gln Gln Lys Pro Gly Ser Ser Pro Lys Arg Trp Ile Tyr Ala Thr TCC AAC CTG GCT TCT GGA GTC CCT GTT CGC TTC AGT GGC AGT GGG TCT GGG ACT
     --- --- --- --- --- --- --- --- --- --- --- --- --- --- --- --- --- ---
  51 Ser Asn Leu Ala Ser Gly Val Pro Val Arg Phe Ser Gly Ser Gly Ser Gly Thr TCT TAC TCT CTC ACA ATC AGC AGA GTG GAG GCT GAA GAT GCT GCC ACT TAT TAC
     --- --- --- --- --- --- --- --- --- --- --- --- --- --- --- --- --- ---
  69 Ser Tyr Ser Leu Thr Ile Ser Arg Val Glu Ala Glu Asp Ala Ala Thr Tyr Tyr TGC CAG CAG TGG ACT AGT AAC CCA CCC ACG TTC GGA GGG GGG GCC AAG CTG GAA
     --- --- --- --- --- --- --- --- --- --- --- --- --- --- --- --- --- ---
  87 Cys Gln Gln Trp Thr Ser Asn Pro Pro Thr Phe Gly Gly Gly Ala Lys Leu Glu ATC AAA|CGT ACG GTG GCT GCA CCA TCT GTC TTC ATC TTC CCG CCA TCT GAT GAG
     --- ---|--- --- --- --- --- --- --- --- --- --- --- --- --- --- --- ---
 105 Ile Lys|Arg Thr Val Ala Ala Pro Ser Val Phe Ile Phe Pro Pro Ser Asp Glu CAG TTG AAA TCT GGA ACT GCC TCT GTT GTG TGC CTG CTG AAT AAC TTC TAT CCC
     --- --- --- --- --- --- --- --- --- --- --- --- --- --- --- --- --- ---
 123 Gln Leu Lys Ser Gly Thr Ala Ser Val Val Cys Leu Leu Asn Asn Phe Tyr Pro
                      [Human Kappa Light Chain Constant]
     AGA GAG GCC AAA GTA CAG TGG AAG GTG GAT AAC GCC CTC CAA TCG GGT AAC TCC
     --- --- --- --- --- --- --- --- --- --- --- --- --- --- --- --- --- ---
 141 Arg Glu Ala Lys Val Gln Trp Lys Val Asp Asn Ala Leu Gln Ser Gly Asn Ser
```

Figure 1B

```
        CAG GAG AGT GTC ACA GAG CAG GAC AGC AAG GAC AGC ACC TAC AGC CTC AGC AGC
        --- --- --- --- --- --- --- --- --- --- --- --- --- --- --- --- --- ---
    159 Gln Glu Ser Val Thr Glu Gln Asp Ser Lys Asp Ser Thr Tyr Ser Leu Ser Ser

ACC CTG ACG CTG AGC AAA GCA GAC TAC GAG AAA CAC AAA GTC TAC GCC TGC GAA
        --- --- --- --- --- --- --- --- --- --- --- --- --- --- --- --- --- ---
    177 Thr Leu Thr Leu Ser Lys Ala Asp Tyr Glu Lys His Lys Val Tyr Ala Cys Glu

GTC ACC CAT CAG GGC CTG AGC TCG CCC GTC ACA AAG AGC TTC AAC AGG GGA GAG
        --- --- --- --- --- --- --- --- --- --- --- --- --- --- --- --- --- ---
    195 Val Thr His Gln Gly Leu Ser Ser Pro Val Thr Lys Ser Phe Asn Arg Gly Glu

Stop
        TGT TGA
        --- ---
    213 Cys ***
```

Amino acid residue numbering is sequential beginning with the amino terminus of the final protein (leader peptide removed).

Figure 2A

DNA and Predicted Amino Acid Sequences
of the "Dimeric" Anti-CD20 Heavy Chain (Version 1)

```
    Start           [Synthetic Leader]
    ATG GGT TGG AGC CTC ATC TTG CTC TTC CTT GTC GCT GTT GCT ACG CGT GTC CTG
    --- --- --- --- --- --- --- --- --- --- --- --- --- --- --- --- --- ---
    Met Gly Trp Ser Leu Ile Leu Leu Phe Leu Val Ala Val Ala Thr Arg Val Leu TCC|CAG GTA CAA CTG CAG CAG CCT GGG GCT GAG CTG GTG AAG CCT GGG GCC TCA
    ---|--- --- --- --- --- --- --- --- --- --- --- --- --- --- --- --- ---
    Ser|Gln Val Gln Leu Gln Gln Pro Gly Ala Glu Leu Val Lys Pro Gly Ala Ser GTG AAG ATG TCC TGC AAG GCT TCT GGC TAC ACA TTT ACC AGT TAC AAT ATG CAC
        --- --- --- --- --- --- --- --- --- --- --- --- --- --- --- --- --- ---
    15  Val Lys Met Ser Cys Lys Ala Ser Gly Tyr Thr Phe Thr Ser Tyr Asn Met His TGG GTA AAA CAG ACA CCT GGT CGG GGC CTG GAA TGG ATT GGA GCT ATT TAT CCC
        --- --- --- --- --- --- --- --- --- --- --- --- --- --- --- --- --- ---
    33  Trp Val Lys Gln Thr Pro Gly Arg Gly Leu Glu Trp Ile Gly Ala Ile Tyr Pro
                    [Murine Anti-Human CD20 Heavy Chain Variable]
        GGA AAT GGT GAT ACT TCC TAC AAT CAG AAG TTC AAA GGC AAG GCC ACA TTG ACT
        --- --- --- --- --- --- --- --- --- --- --- --- --- --- --- --- --- ---
    51  Gly Asn Gly Asp Thr Ser Tyr Asn Gln Lys Phe Lys Gly Lys Ala Thr Leu Thr GCA GAC AAA TCC TCC AGC ACA GCC TAC ATG CAG CTC AGC AGC CTG ACA TCT GAG
        --- --- --- --- --- --- --- --- --- --- --- --- --- --- --- --- --- ---
    69  Ala Asp Lys Ser Ser Ser Thr Ala Tyr Met Gln Leu Ser Ser Leu Thr Ser Glu GAC TCT GCG GTC TAT TAC TGT GCA AGA TCG ACT TAC TAC GGC GGT GAC TGG TAC
        --- --- --- --- --- --- --- --- --- --- --- --- --- --- --- --- --- ---
    87  Asp Ser Ala Val Tyr Tyr Cys Ala Arg Ser Thr Tyr Tyr Gly Gly Asp Trp Tyr TTC AAT GTC TGG GGC GCA GGG ACC ACG GTC ACC GTC TCT GCA|GCT AGC ACC AAG
        --- --- --- --- --- --- --- --- --- --- --- --- --- ---|--- --- --- ---
    105 Phe Asn Val Trp Gly Ala Gly Thr Thr Val Thr Val Ser Ala|Ala Ser Thr Lys GGC CCA TCG GTC TTC CCC CTG GCA CCC TCC TCC AAG AGC ACC TCT GGG GGC ACA
        --- --- --- --- --- --- --- --- --- --- --- --- --- --- --- --- --- ---
    123 Gly Pro Ser Val Phe Pro Leu Ala Pro Ser Ser Lys Ser Thr Ser Gly Gly Thr GCG GCC CTG GGC TGC CTG GTC AAG GAC TAC TTC CCC GAA CCG GTG ACG GTG TCG
        --- --- --- --- --- --- --- --- --- --- --- --- --- --- --- --- --- ---
    141 Ala Ala Leu Gly Cys Leu Val Lys Asp Tyr Phe Pro Glu Pro Val Thr Val Ser
```

Figure 2B

```
        TGG AAC TCA GGC GCC CTG ACC AGC GGC GTG CAC ACC TTC CCG GCT GTC CTA CAG
        --- --- --- --- --- --- --- --- --- --- --- --- --- --- --- --- --- ---
    159 Trp Asn Ser Gly Ala Leu Thr Ser Gly Val His Thr Phe Pro Ala Val Leu Gln

TCC TCA GGA CTC TAC TCC CTC AGC AGC GTG GTG ACC GTG CCC TCC AGC AGC TTG
        --- --- --- --- --- --- --- --- --- --- --- --- --- --- --- --- --- ---
    177 Ser Ser Gly Leu Tyr Ser Leu Ser Ser Val Val Thr Val Pro Ser Ser Ser Leu

GGC ACC CAG ACC TAC ATC TGC AAC GTG AAT CAC AAG CCC AGC AAC ACC AAG GTG
        --- --- --- --- --- --- --- --- --- --- --- --- --- --- --- --- --- ---
    195 Gly Thr Gln Thr Tyr Ile Cys Asn Val Asn His Lys Pro Ser Asn Thr Lys Val

GAC AAG AAA GTT GAG CCC AAA TCT TGT GAC AAA ACT CAC ACA TGC CCA CCG TGC
        --- --- --- --- --- --- --- --- --- --- --- --- --- --- --- --- --- ---
    213 Asp Lys Lys Val Glu Pro Lys Ser Cys Asp Lys Thr His Thr Cys Pro Pro Cys

CCA GCA CCT GAA CTC CTG GGG GGA CCG TCA GTC TTC CTC TTC CCC CCA AAA CCC
        --- --- --- --- --- --- --- --- --- --- --- --- --- --- --- --- --- ---
    231 Pro Ala Pro Glu Leu Leu Gly Gly Pro Ser Val Phe Leu Phe Pro Pro Lys Pro
                        [Human Gamma 1 Heavy Chain Constant]
        AAG GAC ACC CTC ATG ATC TCC CGG ACC CCT GAG GTC ACA TGC GTG GTG GTG GAC
        --- --- --- --- --- --- --- --- --- --- --- --- --- --- --- --- --- ---
    249 Lys Asp Thr Leu Met Ile Ser Arg Thr Pro Glu Val Thr Cys Val Val Val Asp GTG AGC CAC GAA GAC CCT GAG GTC AAG TTC AAC TGG TAC GTG GAC GGC GTG GAG
        --- --- --- --- --- --- --- --- --- --- --- --- --- --- --- --- --- ---
    267 Val Ser His Glu Asp Pro Glu Val Lys Phe Asn Trp Tyr Val Asp Gly Val Glu GTG CAT AAT GCC AAG ACA AAG CCG CGG GAG GAG CAG TAC AAC AGC ACG TAC CGT
        --- --- --- --- --- --- --- --- --- --- --- --- --- --- --- --- --- ---
    285 Val His Asn Ala Lys Thr Lys Pro Arg Glu Glu Gln Tyr Asn Ser Thr Tyr Arg GTG GTC AGC GTC CTC ACC GTC CTG CAC CAG GAC TGG CTG AAT GGC AAG GAG TAC
        --- --- --- --- --- --- --- --- --- --- --- --- --- --- --- --- --- ---
    303 Val Val Ser Val Leu Thr Val Leu His Gln Asp Trp Leu Asn Gly Lys Glu Tyr AAG TGC AAG GTC TCC AAC AAA GCC CTC CCA GCC CCC ATC GAG AAA ACC ATC TCC
        --- --- --- --- --- --- --- --- --- --- --- --- --- --- --- --- --- ---
    321 Lys Cys Lys Val Ser Asn Lys Ala Leu Pro Ala Pro Ile Glu Lys Thr Ile Ser AAA GCC AAA GGG CAG CCC CGA GAA CCA CAG GTG TAC ACC CTG CCC CCA TCC CGG
        --- --- --- --- --- --- --- --- --- --- --- --- --- --- --- --- --- ---
    339 Lys Ala Lys Gly Gln Pro Arg Glu Pro Gln Val Tyr Thr Leu Pro Pro Ser Arg
```

Figure 2C

```
        GAT GAG CTG ACC AAG AAC CAG GTC AGC CTG ACC TGC CTG GTC AAA GGC TTC TAT
        --- --- --- --- --- --- --- --- --- --- --- --- --- --- --- --- --- ---
    357 Asp Glu Leu Thr Lys Asn Gln Val Ser Leu Thr Cys Leu Val Lys Gly Phe Tyr

CCC AGC GAC ATC GCC GTG GAG TGG GAG AGC AAT GGG CAG CCG GAG AAC AAC TAC
        --- --- --- --- --- --- --- --- --- --- --- --- --- --- --- --- --- ---
    375 Pro Ser Asp Ile Ala Val Glu Trp Glu Ser Asn Gly Gln Pro Glu Asn Asn Tyr

AAG ACC ACG CCT CCC GTG CTG GAC TCC GAC GGC TCC TTC TTC CTC TAC AGC AAG
        --- --- --- --- --- --- --- --- --- --- --- --- --- --- --- --- --- ---
    393 Lys Thr Thr Pro Pro Val Leu Asp Ser Asp Gly Ser Phe Phe Leu Tyr Ser Lys

CTC ACC GTG GAC AAG AGC AGG TGG CAG CAG GGG AAC GTC TTC TCA TGC TCC GTG
        --- --- --- --- --- --- --- --- --- --- --- --- --- --- --- --- --- ---
    411 Leu Thr Val Asp Lys Ser Arg Trp Gln Gln Gly Asn Val Phe Ser Cys Ser Val
                                                                        •
        ATG CAT GAG GCT CTG CAC AAC CAC TAC ACG CAG AAG AGC CTC TCC CTG TGT CCG
        --- --- --- --- --- --- --- --- --- --- --- --- --- --- --- --- --- ---
    429 Met His Glu Ala Leu His Asn His Tyr Thr Gln Lys Ser Leu Ser Leu Cys Pro

Stop
        GGT AAA TGA 3'
        --- --- ---
    447 Gly Lys ***
```

The bold dot indicates position of the C to G transversion mutation. The normal TCT codon encoding a serine has been changed to the TGT codon encoding a cysteine amino acid.

Amino acid residue numbering is sequential beginning with the amino terminus of the final protein (leader peptide removed).

Figure 3: Schematic map of expression construct used to transfect CHO 15C9 cell line. Plasmid was linearized by restriction endonuclease digestion with Kpn I and Pac I prior to electroporation.
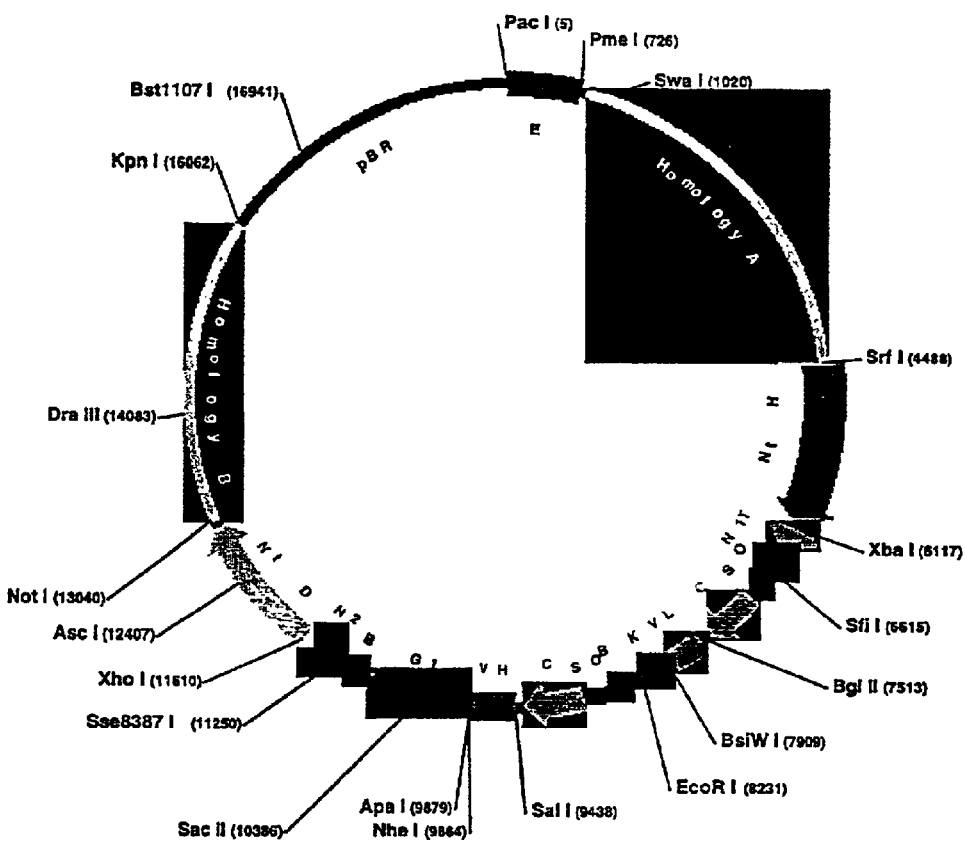

Fig. 4:
Structures of C2B8 (αCD20) Homodimer and C2B8/p5E8 Heterodimer (αCD20/αCD23)
1. C2B8 (-S-S-) C2B8 Homodimer {Disulfide linked}
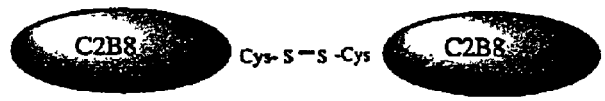
2. C2B8 (-S-) C2B8 Homodimer {Thioether linked}
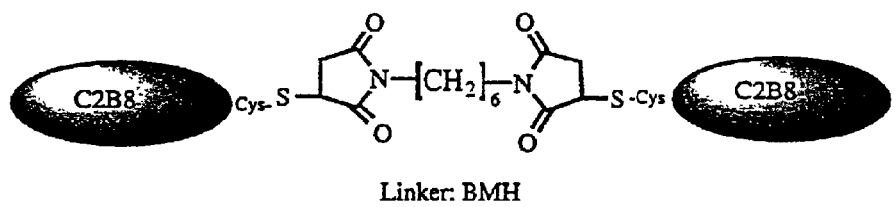
Linker: BMH
3. C2B8 (-S-) p5E8 Heterodimer {Thioether linked}
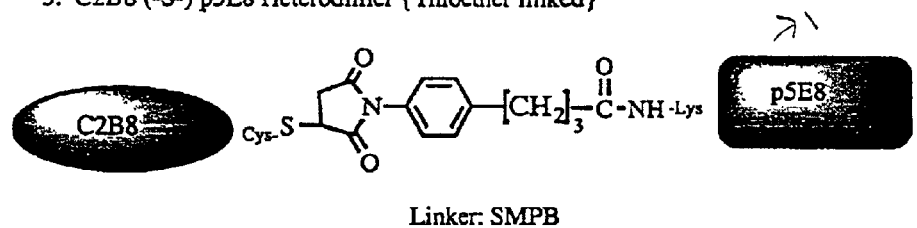
Linker: SMPB

Fig. 5
SDS/PAGE Non-Reducing Gel Comparing C2B8 (-s-s-) Homodimers and C2B8/p5E8 (-s-) Heterodimers to Starting Material Mab protein was analyzed using a 4%-20% SDS/Tris-Glycine gel under non-reducing conditions. Except for lane 2, each well received 1 ug/ml Mab protein. Individual protein bands were visualized with XXXblue stain.

MW : MW Markers
Lane 1: C2B8/SH Tissue Culture
Lane 2: C2B8/SH, Lot #: 2058-29 pA purified, (2 ug/ml)
Lane 3: C2B8/SH, Lot #: 2058-29 pA purified Lane 4: C2B8 (-s-s-) Homodimer, Lot # 1966-76c before HPLC purification
Lane 6: C2B8/p5E8 (-s-) Heterodimer Lot#:1977-76a 300kDa HPLC Fraction
Lane 7: C2B8, clinical Lot #:0113
Lane 8: p5E8 monomer, clone H24-31

Fig. 6
SDS/PAGE Reducing Gel Comparing C2B8 (-s-s- and -s-) Homodimers and C2B8/p5E8 (-s-) Heterodimers to Starting Material Mab protein was analyzed using a 4%-20% SDS/Tris-Glycine gel under reducing conditions. Mab protein was reduced using 2-mercaptoethanol and heat (90°C, 10 min) before SDS/PAGE. Individual protein bands were visualized with Comassie blue stain.

Lanes 1: MW Markers
Lane 2: p5E8 (clone H24-31), pA purified
Lane 3: C2B8/SH, Lot #: 2058-29 pA purified,
Lane 4: C2B8/SH, Lot #: 2058-29 Reduced DTT Lane 5: C2B8 (-s-s-) Homodimer, Lot # 1966-76c 300kDa HPLC Fraction
Lane 6: C2B8/p5E8 (-s-) Heterodimer Lot#:1977-76a 300kDa HPLC Fraction
Lane 7: C2B8 (-s-) Homodimer Lot #: 1966-76b 300kDa HPLC Fraction

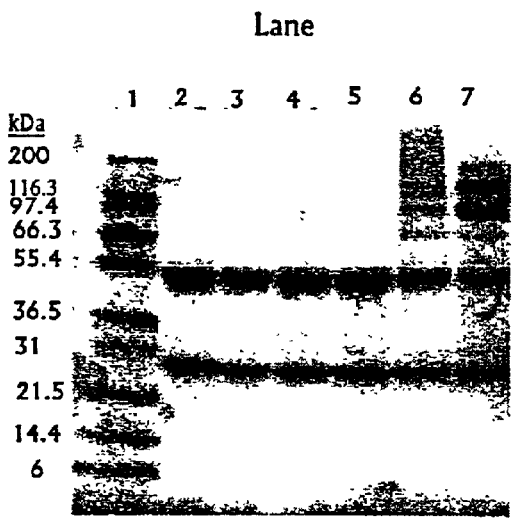

HPLC Analysis of C2B8 Homodimers

Table 1

| Antibody | Percent | | |
|---|---|---|---|
| | Monomer | Dimer | Aggregate |
| C2B8 | 97.2 | 2.8 | |
| C2B8/SH | 77.9 | 17.5 | 4.6 |
| Dimer (-s-s-) | 40.9 | 89.4 | 14.8 |
| Dimer (-s-) | 66.2 | 27.9 | 3.6 |

HPLC Analysis of C2B8/p5E8 Heterodimers (αCD20/αCD23 Dimer)

Table 2

| Antibody | Percent | | |
|---|---|---|---|
| | Monomer | Dimer | Aggregate |
| C2B8/SH | 82.5 | 12.5 | 5 |
| p5E8 | 99.8 | 0.2 | |
| Heterodimer | 34.5 | 26 | 39.5 |
| purified Dimer | 3.5 | 96.5 | |

Binding of C2B8 (s-s-) Homodimer to CD20 Positive
Cell Lines: SKW and SB

Fig 10: Competitive Binding Assay of C2B8 and C2B8 (-s-s-) Homodimer on SKW cells Binding of αCD20/αCD23 Heterodimer
(C2B8/p5E8, Lot #: 1966/84)
to SKW and DHL-4 Cell Lines Fig: 12
Binding of aCD20 C2B8 Homodimer and aCD20/aCD23 C2B8/p5E8 Heterodimer to SKW cells (CD20+/CD23+)

Apoptotic Activity of C2B8 (-s-s-) Homodimer

Apoptotic Activity of C2B8/p5E8
(-s-) Hetrodimer

Fig: 17:
Growth Inhibition of B-Lymphoma CD20/CD23 Positive Cell Lines (SB and SKW) after 96 hour Continuous Exposure to MAb
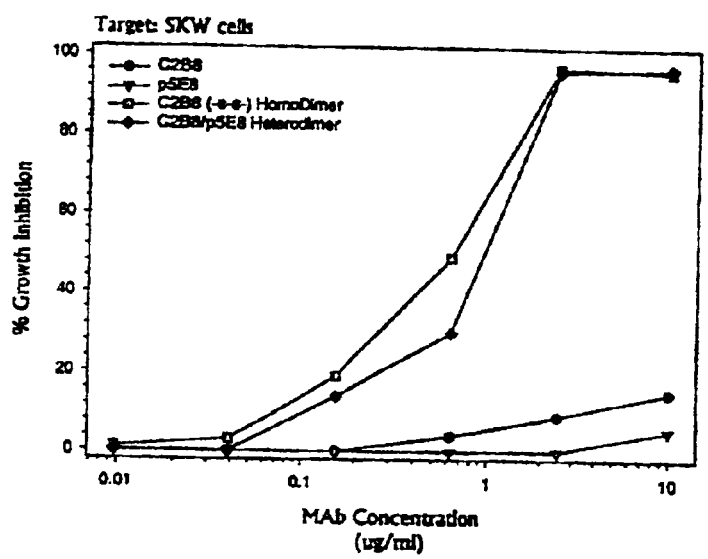
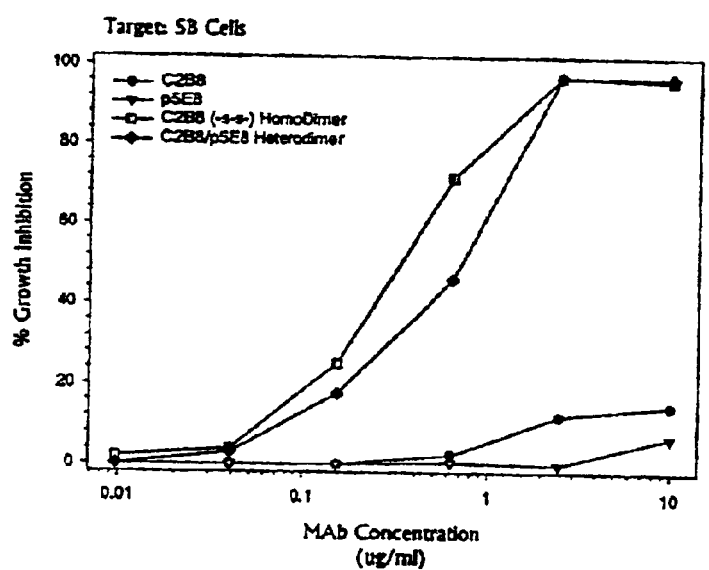

PRODUCTION OF TETRAVALENT ANTIBODIES

FIELD OF THE INVENTION

The present invention generally relates to a novel process for the preparation of biologically active antibody dimers and a pharmaceutically acceptable compositions containing such dimers. These dimers can be composed of two antibody molecules having the same antigen binding specificity and linked through a reducible, disulfide, or a non-reducible thioether, bond (homodimers) or, alternatively, can be composed of two different antibody molecules having binding specificity for two distinct antigens (heterodimers). The subject antibody dimers are useful for inducing hyper-cross-linking of membrane antigens. The present invention further relates to the use of biologically active antibody dimers for the preferential killing or inhibition of selected cell populations in the treatment of diseases such as cancer and autoimmune disorders.

BACKGROUND OF THE INVENTION

Monoclonal antibodies were once thought to be an ideal way to target malignant tissues, by delivering a killing agent, while leaving healthy tissue intact. However, their clinical potential is limited due to the need to covalently couple the killing agent to the monoclonal antibody. Thus, in an effort to alleviate such limitations, bispecific antibodies were developed, which remain bivalent, but are specific for a target cell on one arm of the antibody and a killing agent on the other arm. The killing agent can be a toxin, a drug, a chelated radioisotope, or, more likely, a cytotoxic effector cell.

Monoclonal antibodies can also show therapeutic activity against specific cells, e.g., malignant tissues based on the interaction of the Fc portion of the antibody heavy chain with other components of the immune system, such as the complement cascade or by binding to Fcγ receptors or various cytotoxic effector cell types.

Another means of effecting cell death comprises inducing the cross-linking of membrane antigens. Previous studies have indicated that antibody cross-linking of membrane B-cell markers (e.g., surface IgM, Valentine et al., *Eur. J. Immunol.* 22:3141 (1992); and MHC class II, Newell et al., *PNAS* 90:10459 (1993)) can inhibit malignant B cell proliferation and in many cases induce apoptosis (e.g., programmed cell death) in vitro.

Shan et al. (*Blood* 91:1644–1653) demonstrated that hyper-cross-linking of the CD20 antigen, by using the murine 1 F5 antibody cross-linked with a goat anti-mouse IgG, inhibited growth of several human B-lymphoma cell lines in vitro. Similar results have now been published for both CD19 and CD22 when cross-linking of membrane bound MAb was amplified with a anti-mouse IgG (Chaouchi et al., *J. Immunol.* 154:3096 (1995)).

It may be possible that hyper cross-linking of these surface membrane markers could augment the existing anti-tumor activities of MAb's like C2B8, a chimeric monoclonal antibody specific for CD20, and increase therapeutic effectiveness. Therefore, molecules that can induce cell death in a pharmaceutically acceptable format would potentially provide an attractive therapeutic agent for immunotherapy of neoplastic disease.

Apparently with that goal in mind, Wolff et al. (*Cancer Res.* 53:2560–2565 (1993)) and Ghetie (PNAS 94:7509–7514 (1997)) have reported the chemical synthesis of several IgG/IgG homodimers to carcinoma associated surface antigen (BR96 and HER-2). The Ghetie dimers also included antibodies to several human B-cell markers (CD20, CD19, CD21, CD22). In this approach, one portion of the molecule was functionalized using a linker designed to introduce a reactive thiol on the antibody, while the other Ab portion used a linker to introduce a maleimido group. When purified from unreacted linkers and mixed together, the two antibodies complex by formation of a thioether (non-reducible) bridge that links the two IgG molecules, and forming a 300 kDa, tetravalent antibody $(C_2H_2)_{2g}$ molecule.

However, unfortunately, the yields of the 300 kDa IgG-homodimer were very low (20–25%) and were similar or lower than "spontaneously" formed CD19 homodimer, which ranged from 20–30% (Ghetie et al., *PNAS*94:7509–7514 (1997)).

Reducing SDS-PAGE gels of purified homodimer showed only a small percentage was linked via a thioether bond, indicating most of the dimers formed using this methodology may have been naturally occurring or mediated through disulfide bridging. Nevertheless, all of the purified dimers were growth inhibitory, although only the anti-carcinoma (Her-2) dimer and not homodimers directed against B cell markers CD19, CD20, CD21, CD22 were reported to be apoptotic. Additionally, the anti-CD19 homodimer was tested in animal models and shown to have anti-tumor activity. However, there is a need in the art for a more efficient method for producing homodimers, in particular for homodimers or heterodimers that are capable of initiating apoptosis, e.g., in proliferating malignant B-cells populations.

In the present invention, two monoclonal antibodies were used: a mouse/human chimeric antibody specific for CD20 (C2B8), and a Primatized® antibody specific for CD23 (p5E8). Low grade and aggressive B-cell lymphomas express the B cell antigens CD20 and CD23. CD20 is a non-glycosylated 35 kDa B-cell membrane protein associated with intracellular signaling, B-cell differentiation and calcium channel mobilization (Clark et al., *Adv. Cancer Res.* 52:81–149 (1989); Tedder et al., *Immunol. Today* 15:450–54 (1994)). The antigen appears as an early marker of the human B-cell lineage, and is ubiquitously expressed at various antigen densities on both normal and malignant B cells. However, the antigen is absent on stem cells or pre B cell populations, as well as on the fully matured plasma cell, making it a good target for antibody mediated therapy. CD23 is the low affinity receptor for IgE. Antibodies to CD23 have been suggested to be useful for treating allergic and inflammatory responses. In fact, IDEC Pharmaceuticals, Inc., the assignee of this application, has an application pending relating to the use of an anti-CD23 antibody of the IgG1 isotype for therapeutic usage. Of importance herein, CD23 is expressed on B-cells, and particularly by B-cell lymphoma cells.

While only a small fraction of the CD20 antigen is expressed on the surface membrane, MAb's binding to the extracellular domain have had variable activities in promoting or inhibiting B cell function. For example, the anti-CD20 MAb, IF5, was originally shown to activate resting ($G_0$) B-cells into ($G_1$/S/$G_2$) proliferating populations (Clark et al., *PNAS, USA,* 82:1766–70 (1985)). Additionally, Holder et al. (*Eur. J. Immunol.* 25:3160–64 (1995) demonstrated that Mab IF5 cross-linking of the CD20 surface antigen protected proliferating tonsular B cells from undergoing apoptosis (programmed cell death) in vitro. In contrast, the anti-CD20 antibody B1 that binds to a different epitope than IFS (Tedder et al., *Immunol. Today* 15:450 (1994), was not stimulatory for resting B cell populations (Tedder et al., *Eur. J. Immunol.* 16:881 (1986)).

Despite differences in activity using normal B cell populations, murine anti-CD20 MAb's (e.g., IF5, B1, B20 and 2H7) had no effect on growth inhibition of proliferating human (CD20+) lymphoma cell lines in vitro, but in vivo showed tumor growth inhibition using human lymphoma mouse xenograft models (Press et al, *Blood* 69:584–591 (1987); Shan et al., *Blood* 91:1644–1653 (1998); Funakoshi et al., *J. Immunol.* 19:93–101 (1996); Hooijberg et al., *Cancer Res.* 55:840–846 (1995); and Ghetie et al., *PNAS* 94:7509–7514 (1997)). The mechanism mediating anti-tumor activity remains unclear but may be mediated through complement dependent cell killing (CDC) or antibody dependent cell killing (ADCC), both of which are dependent on activation of host cell mechanisms through the Fc portion of the MAb after CD20 binding. Indeed, Funakoshi et al. (*J. Immunol.* 19:93–101 (1996)) has shown that the anti-tumor activity of 2H7 in vivo was blocked when Fc receptor was blocked or with a F(ab)$_2$ antibody.

The chimeric MAb used in the present invention (C2B8) was developed at IDEC Pharmaceuticals Corporation for treatment of human B cell lymphoma (Reff et al., *Blood* 83:4350445 (1994)). C2B8 originated from the murine antibody 2B8 and was cloned and expressed as a 150 kDa IgG monomer in Chinese Hamster Ovary cells. MAb C2B8 maintains the 2B8 murine variable region coupled to the human gamma 1 heavy chain and human K light chain constant regions. Like its murine counterparts, C2B8 was not growth inhibitory and does not induce apoptosis of human lymphoma cell lines in vitro, but does demonstrate anti-tumor activity when tested in vivo using murine xenograft animal models.

Chimeric C2B8 efficiently binds human complement, has strong FcR binding, and can efficiently kill human lymphocytes in vitro via both complement dependent (CDC) and antibody dependent (ADCC) mechanisms (Reff et al., *Blood* 83:435–445 (1994)). C2B8 was also strongly depleting of B cells in human Phase I/II clinical trials, but was nevertheless shown to be safe and effective with most side effects infusion related (Maloney et al., *Blood* 84:2457–2466 (1994) and Maloney et al., *JCO* 15(10):3266 (1997)).

The antibody showed an overall response rate of 48% in patients with low grade or follicular lymphoma (McLaughlin et al., *JCO*, in press). However, the response rate decreased dramatically (34%) in chemo-resistant patients who failed to respond to their last chemotherapy regime (McLaughlin et al., *Proc. Am. Soc. Clin. Oncol.* 16:16a (Abstr. 55) (1997)). Additionally, the antibody showed poor activity in patients with type A histology or with chronic lymphocytic leukemia (CLL). Therefore, the need to increase the effectiveness of antibody immunotherapy and, specifically, using C2B8 or CD23 antibody therapy remains a high priority in the treatment of human leukemia and lymphoma patients. The anti-CD23 antibody exemplified in the methods herein was also developed by IDEC and is a primatized anti-CD23 antibody of the IgG1 isotype.

OBJECTS OF THE INVENTION

Based on the foregoing, an object of the invention is to provide novel therapeutic agents, in particular antibody dimers for use in antibody therapies.

More specifically, it is an object of the invention to provide novel antibody dimers having specificity to CD23 and/or CD20 antigen.

It is a more specific object of the invention to provide an efficient method for producing stable antibody dimers, especially IgG/IgG homodimers.

It is another object of the invention to provide novel therapies involving the administration of antibody dimers.

It is a more specific object of the invention to provide novel methods for treating cancer, and autoimmune or allergic disorders by administering antibody dimers.

It is another object of the invention to provide novel therapeutic compositions containing antibody dimers, in particular for treatment of cancers, allergic disorders, autoimmune disorders.

BRIEF DESCRIPTION OF THE FIGURES

FIG. 1 contains DNA and predicted amino acid sequences [SEQ ID NOS. 1&2] of a "dimeric anti-CD20 light chain (version 1).

FIG. 2 contains DNA and predicted amino acid sequences [SEQ ID NOS. 3&4] of a "dimeric" anti-CD20 heavy chain (version 1).

FIG. 3 is a schematic map of expression construct used to express the subject antibodies.

FIG. 4 contains structures of C2B8 (αCD20) homodimer and C2B8/p5E8 heterodimer (αCD20/αCD23).

FIG. 5 contains SDS/PAGE results comparing C2B8 (-s-s-) homodimers and C2B8/p5E8 (-s-) heterodimers to starting material.

FIG. 6 contains SDS/PAGE results comparing C2B8 (-s-s- and -s-) homodimers and C2B 8/p5E8 (-s-) heterodimers to starting material.

FIG. 17 shows growth inhibition of B-lymphoma CD20/CD23 positive cell lines (SB and SKW) after 96 hours continuous exposure to MAb.

DETAILED DESCRIPTION OF THE PREFERRED EMBODIMENTS

Figure 7:
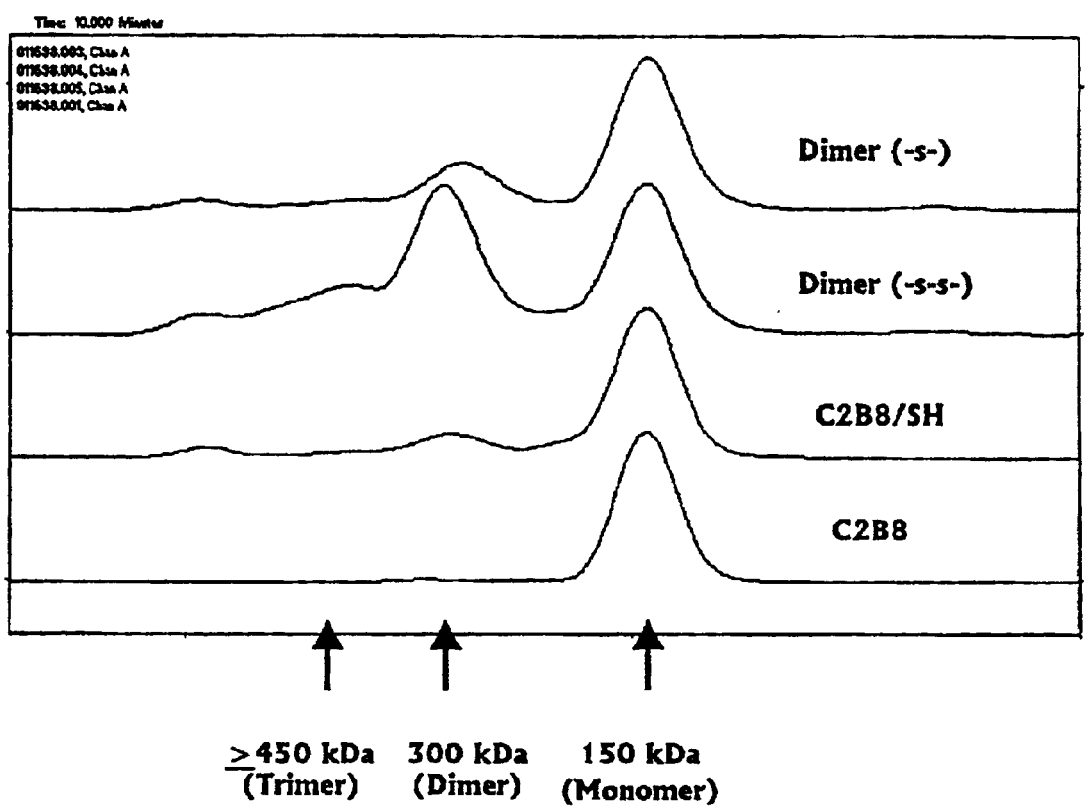
FIG. 7 contains HPLC analysis of C2B8 homodimers.

The following description will enable a person skilled in the art to which this invention pertains to make and use the invention, and sets forth the best modes contemplated by the inventors of carrying out their invention.

As discussed, the present invention generally relates to a process for the preparation of biologically active antibody dimers and pharmaceutical composition containing such antibody dimers. The present invention further relates to the use of biologically active antibody dimers for the preferential killing or inhibition of selected cell populations in the treatment of diseases such as cancer and autoimmune disorders.

Previously, homodimers were chemically generated from naturally occurring monoclonal antibodies by using chemical cross-linkers to introduce a thioether bond between the two IgG antibodies (Ghetie, PNAS 94:7509–7514 (1997)). Because the dimers are formed using chemically functionalized antibodies, one cannot control where the thioether linkage occurs. As a result, the Ghetie method yielded a low amount of homodimers and resulted in a mixture of naturally occurring, disulfide linked homodimers and the chemically generated thioether linked homodimers.

Because of the need for a method which produces an increased yield and chemical purity of IgG homodimers, applicants set out to develop the method of the present invention. The present invention is distinguished from Ghetie by the use of monoclonal antibodies which have had a cysteine residue genetically engineered at a specific site on the $F_c$ arm of the antibody, thereby eliminating the need to chemically introduce a reactive thiol group.

The method of the present invention increases yield of homodimer formation to 40–50% of the starting material, and is applicable for preparing either disulfide or thioether linked antibody homodimers, preferably IgG/IgG homodimers. Additionally, preparation of thioether linked homodimer was more efficient than the Ghetie method as determined by SDS-PAGE (reducing) gels. Because of the high yield and efficiency of thioether linked homodimers, this method, unlike the Ghetie method, can also be used for preparing antibody heterodimers (preferably IgG/IgG heterodimers), in which each antibody arm is directed against different antigens.

Also, surprisingly and quite unexpectedly, when compared to the Ghetie anti-CD20 dimers using MAb 2H7, the C2B8 dimers using this present method (homodimers and heterodimers) were capable of initiating apoptosis in proliferating malignant B-cell populations. More importantly, these dimers were strongly growth inhibitory for lymphoma cells in culture, showing a 200-fold increase in potency over dimers prepared according to the method of Ghetie. Homodimers (disulfide linked) were also evaluated in animals and shown to have better therapeutic activity than the parent molecule C2B8.

The monoclonal antibodies used for the present invention can be any monomeric antibody, and need not be limited to IgG. Furthermore, they may be from any mammalian host. Although in the examples the cysteine was engineered at position 444 of the heavy chain, the location of the cysteine is not limited to this position, and the invention embraces incorporation of cysteine at other sites. In fact, other sites on the antibody may be better suited for cysteine placement. In this regard, the placement of cysteine at position 444 may not be preferred because the cysteine molecule (one on each arm) is close in proximity to the cysteine on the neighboring heavy chain such that an intrachain disulfide bond may form. Therefore, it may be preferable to place cysteine at a different site, e.g., on the outside loop of a domain where the cysteine molecules would physically be further apart. Thereby, the potential for the formation of intrachain disulfide bonds would potentially be eliminated or minimized.

Three specifically contemplated alternative positionings with the anti-CD20 antibody 2B8 could include replacing the serine residue at position 416, the glutamine residue at position 420, or the glycine residue at position 421. These sites have been selected cognizant of the fact that one desires to enhance dimer formation yet retain the antibody affinity and effector functions as much as possible. Also, it is anticipated that other sites may also provide for effective dimer formation.

It is desirable to eliminate intrachain disulfide bonds so that the cysteine thiol will be free to form bonds with thiol-reactive groups on other antibodies (via disulfide or thioether linkage). These reactions can include alkylation of the cysteine thiol by maleimides, oxidation of two adjacent thiol groups to a disulfide bond, or through disulfide interchain bonds with pyridyl protected disulfides.

Various molecular biological techniques (including, but not limited to site directed mutagenesis, PCR mutagenesis, random mutagenesis, restriction fragment subcloning, DNA synthesis, etc.) can be employed by one skilled in the art to insert the cysteine at the appropriate site with the resultant antibody molecule. In the examples that follow, site directed mutagenesis was used. Production of the recombinant antibody then, in general, includes introduction of a recombinant gene encoding an antibody heavy chain into any suitable host cell together with a recombinant gene encoding an appropriate antibody light chain. The transfected cells can either be grown in vitro or in vivo.

As discussed above, placement of the engineered cysteine at position 444 of the heavy chain resulted in intrachain disulfide formation. Therefore, the molecule must be partially reduced before dimerization can proceed. It is anticipated that changing the placement of the introduced cysteine would eliminate this step. However, for these engineered molecules, the disulfide bond (S—S) formed between the neighboring cysteine molecules on the genetically engineered antibody molecules must be reduced to the free thiol. Applicants have chosen to partially reduce the antibody molecules using dithiothreitol (DTT) in order to selectively expose specific thiols. Partial reduction at 37° C. requires a range of reducing agent concentration from about 1 to 3 molar excess.

However, these reaction conditions can be modified. For example, the reaction can be effected at lower temperatures or with other reducing agents, such as mercaptoamines or mercaptoethanol. These reaction conditions may require a higher molar excess, which may be readily determined using routine experimentation by one of skill in the art. Under the limiting conditions used, these agents will reduce the most accessible cysteine first. Thus, it is important that the genetically engineered cysteine molecule be positioned correctly and be readily available for reduction. This will increase the likelihood that the genetically engineered cysteine will be the molecule forming bonds with cysteines or other thiol reactive groups on other antibody molecules. Additionally, the introduced cysteine must be positioned correctly on the heavy chain so as to not interfere with FcγR binding or complement activation. This can be determined by trial and error experimentation.

The methods of the present invention produce either dimers formed by disulfide bonds or dimers formed by thioether linkage. In the case of disulfide bonds, the bonds form naturally between the thiol groups on the cysteine. For thioether linkage, a maleimido crosslinker (which is thiol reactive) is added to the antibodies which forms a bridge between the two antibody molecules. There are a variety commercially available of maleimido cross-linkers which can be used for the present invention. These cross-linkers bind on one side to a thiol group and on the other side to any of a variety of molecules (for example, lysine, a carboxyl group, etc.) which are naturally present on an antibody molecule. In this way, a dimer can be formed between an antibody which has been modified to contain a cysteine molecule at a specific position and another antibody which has not been modified. By using special conditions (i.e. purifying the selectively reduced MAb by applying it to a PD-10 column and equilibrating with deoxygenated normal saline containing sodium citrate (10 mM) and EDTA (1 mM)), which discourage the formation of homodimers via a disulfide bond, one can be assured that only dimers formed by a thioether linkage are produced.

Unlike the Ghetie method, which results not only in chemically induced dimers but also naturally occurring dimers, the method of the present invention produces very little if any naturally occurring dimers, and thus obtains a high yield of the desired dimer. The dimers produced by the present invention also, surprisingly, enhanced apoptotic activity of B cells from chronic lymphocytic leukemia (CLL) patients. Previously it was thought that only B cell lymphoma cells expressed enough CD20 to elicit complement activation when antibody dimers were used. CLL B cells express low levels of CD20, and previous attempts to activate complement mediated killing of CLL B cells were unsuccessful. Therefore, it was surprising to discover that the dimers produced by the method of the present invention were capable of inducing apoptosis of B cells from CLL patients.

The anti-CD23 antibodies produced by the subject invention can be used for treatment of conditions including the following:

Allergic bronchopulmonary aspergillosis; Allergic rhinitis Autoimmune hemolytic anemia; Acanthosis nigricans; Allergic contact dermatitis; Addison's disease; Atopic dermatitis; Alopecia greata; Alopecia universalis; Amyloidosis; Anaphylactoid purpura; Anaphylactoid reaction; Aplastic anemia; Angioedema, hereditary; Angioedema, idiopathic; Ankylosing spondylitis; Arteritis, cranial; Arteritis, giant cell; Arteritis, Takayasu's; Arteritis, temporal; Asthma; Ataxia-telangiectasia; Autoimmune oophoritis; Autoimmune orchitis; Autoimmune polyendocrine failure; Behcet's disease; Berger's disease; Buerger's disease; bronchitis; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cogan's syndrome; Cold agglutinin disease; CREST syndrome; Crohn's disease; Cryoglobulinemia; Cryptogenic fibrosing alveolitis; Dermatitis herpetifomis; Dermatomyositis; Diabetes mellitus; Diamond-Blackfan syndrome; DiGeorge syndrome; Discoid lupus erythematosus; Eosinophilic fasciitis; Episcleritis; Drythema elevatum diutinum; Erythema marginatum; Erythema mulfiforme; Erythema nodosum; Familial Mediterranean fever; Felty's syndrome; Fibrosis pulmonary; Glomerulonephritis, anaphylactoid; Glomerulonephritis, autoimmune; Glomerulonephritis, post-streptococcal; Glomerulonephritis, post-transplantation; Glomerulopathy, membranous; Goodpasture's syndrome; Graft-vs.-host disease; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis X; Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; lupus; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythematosus; Pemphigus foliaceus; Pemphigus vulgaris; Pigeon breeder's disease; Pneumonitis, hypersensitivity; Polyarteritis nodosa; Polymyalgia rheumatic; Polymyositis; Polyneuritis, idiopathic; Portuguese familial polyneuropathies; Pre-eclampsia/eclampsia; Primary biliary cirrhosis; Progressive systemic sclerosis (Scleroderma); Psoriasis; Psoriatic arthritis; Pulmonary alveolar proteinosis; Pulmonary fibrosis, Raynaud's phenomenon/syndrome; Reidel's thyroiditis; Reiter's syndrome, Relapsing polychrondritis; Rheumatic fever; Rheumatoid arthritis; Sarcoidosis; Scleritis; Sclerosing cholangitis; Serum sickness; Sezary syndrome; Sjogren's syndrome; Stevens-Johnson syndrome; Still's disease; Subacute sclerosing panencephalitis; Sympathetic ophthalmia; Systemic lupus erythematosus; Transplant rejection; Ulcerative colitis; Undifferentiated connective tissue disease; Urticaria, chronic; Urticaria, cold; Uveitis; Vitiligo; Weber-Christian disease; Wegener's granulomatosis; Wiskott-Aldrich syndrome.

Of these, the preferred indications treatable or presentable by administration of anti-CD23 antibodies include allergic rhinitis, atopic dermatitis; eczema; Job's syndrome, asthma; and allergic conditions; inflammatory diseases and conditions.

The antibody molecules produced by the method of the present invention can be used in pharmaceutical compositions for any application wherein antibodies are therapeutically beneficial, e.g., the treatment of cancer and autoimmune disorders in mammals, especially humans. The genetically engineered antibodies of the present invention can be formulated according to known methods to prepare pharmaceutically useful compositions such as by admixture with a pharmaceutically acceptable carrier vehicle. Suitable vehicles and their formulation are described, for example, in Remington's Pharmaceutical Sciences (16" Ed., Osol, A. Ed., Mack Easton Pa. (1980)). To form a pharmaceutically acceptable compositions suitable for effective administration, such compositions will contain an effective amount of antibody, either alone, or with a suitable amount of carrier vehicle, e.g., a buffered saline solution.

The therapeutic compositions of the invention will be administered to an individual in therapeutically effective amounts. That is, in an amount sufficient to treat a particular condition, e.g., a cancer or an autoimmune disorder. The effective amount will vary according to the weight, sex, age and medical history of the individual. Other factors include the severity of the patient's condition, the mode of administration, and the like. Generally, the compositions will be administered in dosages ranging from about 0.01 to about 2 picomoles/ml, more generally about 0.0001 to about 200 picomoles/ml.

The pharmaceutically prepared compositions may be provided to a patient by any means known in the art including oral, intranasal, subcutaneous, intramuscular, intravenous, intraarterial, parenteral, etc.

Having now generally described the invention, the following examples are offered by way of illustration only and are not intended to be limiting unless otherwise specified.

EXAMPLE 1

Production of Genetically Engineered C2B81SH (NTB #:2012–85 and 2092/64)

a. Generation of C2BS/SH Anti-CD20 (Version 1) Cell Line:

It has been previously demonstrated by Shopes (J. Immunol. 148(9):2918–2922 (1992), and Shopes et al, WO 91/19515, Dec. 26, 1991) that "tail-to-tail" dimeric immunoglobulin $(L2H_2)_2$ molecules can be induced through formation of a disulfide linkage between individual $L2H_2$ immunoglobulin molecules. A similar approach was used by Caron et al. (J. Exp. Med. 176:1191–95 (1992)). Both groups artificially introduced a cysteine four amino acids from the carboxyl end of the heavy chain, by replacing the serine residue at position 444 of the H-chain with a cysteine.

In an effort to create a dimeric anti-CD20 immunoglobulin, applicants similarly introduced a cysteine residue within the chimeric anti-CD20 antibody, C2B8. FIG. 1 shows the nucleotide and predicted amino acid sequence of the murine anti-human CD20 light chain variable domain fused to the human kappa light chain constant domain. FIG. 2 shows the nucleotide and predicted amino acid sequence of the murine anti-human CD20 heavy chain variable domain fused to the human gamma 1 heavy chain constant domain.

Through the use of conventional in vitro site directed mutagenesis applicants effected a transversion mutation C to G within the plasmid DNA (FIG. 3). This IDEC proprietary expression construct (Reff et al., U.S. patent application Ser. No. 08/819,866, filed Mar. 14, 1997, now U.S. Pat. No. 5,830,698) encodes the anti-CD20 immunoglobulin light and heavy chains, as well as sequences necessary for homologous integration into a proprietary CHO cell line Reff et al. IBID). followed by dominant selection with G418 and/or methotrexate. The affect of this nucleotide mutation is to change the codon second base, thereby encoding a cysteine residue substituted for the normal serine residue at position 445 near the gamma 1 heavy chain carboxyl terminus (see FIG. 2).

This expression construct (FIG. 3) was transfected into IDEC's CHO cell line designated 15C9 which was originally derived from CHO DG-44 (Urlaub et al., Som. Cell Mol. Gen. 12(6):555–566, 1986). Following selection with G418, a high level immunoglobulin producing clone, termed 3F9, was isolated. 3F9 produces and secretes into the cell growth medium, roughly 3.4 pg/cell/day of immunoglobulin. The ELISA assay of immunoglobulin productivity measures $L_2H_2$ immunoglobulin molecules irrespective of their monomeric, dimeric or oligomeric configuration. As evidenced by western blot analysis, the majority of the secreted immunoglobulin is monomeric (L2H2). However, a small percentage is in the dimeric and larger oligomeric forms.

The 3F9 cell line was then selected in 5 nM methotrexate. Growth in methotrexate can be used to artificially induce gene amplification (Alt et al., J. Biol. Chem. 253:1357–1370 (1978)) and expression of the plasmid encoded DHFR gene. Concomitantly, the linked immunoglobulin light and heavy chain genes will also be amplified resulting in increased immunoglobulin gene expression and higher immunoglobulin protein production. Through gene amplification, we were able to effectively induce an increase in total anti-CD20 production levels. Following selection, the clone designated 3F9-50B 11 was identified. 3F9-50B11 produces roughly 6.3 pg/cell/day of anti-CD20 protein.

b. Purification C2B8/SH (Ver. I):

C2B8/SH was purified from growth media (12 L at 15 mg/L) using protein A (pA) column Chromatography. Sodium azide (0.01% final concentration) was added to the C2B8/SH antibody containing media and pH adjusted to 7.5 with ION NaOH. The material was applied to a PBS washed pA affinity column (15 ml column, Bioprocess Ltd.) at approximately 3 ml/min. in a 4–8° C. cold room, followed by washing with at least 5 column volumes PBS (100 ml). Antibody was eluted from the pA column with 100 ml Sodium Citrate (0.1 M, pH 3.5), and immediately neutralized to pH 7 with 1M Tris Base. C2B8/SH (pA purified) was dialyzed against PBS (1000 ml×4 changes over 3 days), concentrated to approx. 10 mg/ml under Nitrogen (50 psi) in an Amicon stirred cell concentrator (MWCO 30,000), and filter (0.2 μm) sterilized. The pA purified C2B8/SH material was stored at 4° C. Protein concentration was determined spectrophotometrically: MAb (mg/ml)=[Absorbence at OD280]×[dilution factor]/1.7.

c. Characterization C2B8 Homodimer:

C2B8/SH IgG (150 kDa) having a genetically engineered thiol group in the antibody heavy chain is able to form a 300 kDa IgG/IgG homodimer through intermolecular disulfide linkage. The amount of homodimer formed was determined using analytical HPLC and non-reducing SDS/PAGE. Analytical size-exclusion high performance liquid chromatography (SE-HPLC) was performed using a Beckman 126 HPLC system operating isocratically at a flow rate of 1.0 ml/min., with a mobile phase consisting of 100 mM sodium phosphate, 150 mM sodium chloride, pH 6.8. The separation was performed at room temperature using a 7.8×300 mm BioSil SEC 250–5 column (Bio-Rad Catalog #125-0062) monitored by Absorbence at 280 nm. Molecular weights were approximated by comparison to an external Bio-Rad Gel Filtration Standard (Bio-Rad Catalog #151-1901).

Non-Reducing SDS/PAGE gels of CHO secreted C2B8/SH (FIG. 5, Lane 1) showed a major protein band at 150 kDa (IgG) and HPLC analysis of several preparation showed <6% IgG/IgG homodimer (300 kDa) in MAb containing growth medium. After pA purification and concentration, three major protein bands were observed (FIG. 5, Lane 2). Molecular weight determination by HPLC showed the three protein peaks at 150 kDa (80.3%), 300 kDa (14.9%) and >450 kDa (4.8%). HPLC results from several C2B8/SH pA purifications showed homodimer ranges from 12.5–17.9% (FIGS. 7, 8) which was comparable to the amount of MAb homodimers synthesized by Ghetie et al. (PNAS, USA 49:7509–7514 (1997)), who used hetero-bifunctional cross-linking agents to chemically couple the IgG monomers.

The reactive thiol concentration (free SH content) remaining after dimerization was estimated using the method of Ellman et al. (Anal. Biochem. 94:75–81 (1979)). Despite the observation that >80% of the C2B8/SH remained monomer after dimerization, very little reactive thiol was detected (<0.2 SH groups per MAb), indicating that the genetically introduced thiol on the IgG heavy chain was blocked, most likely through intermolecular disulfide bridging

EXAMPLE 2

(Ntb #:1966/84): Selective Reduction of C2B8/SH and Preparation of C2B8, Disulfide Linked, Homodimer (FIG. 4.1)

To increase the percentage of dimer in the C2B8/SH preparation, pA purified material was partially reduced with a 2-fold molar excess of dithiothreitol (DTT), concentrated, and allowed to form antibody dimers in PBS under normal atmospheric conditions. MAbs partially reduced using DTT for use in preparing affinity columns (Goldenberg et al., Bioconj. Chem. 2:275–280 (1991)) or for immunoconjugate preparations (Siegall et al., *Bioconj. Chem.* 3:302–307 (1992), Willner et al., *Bioconj. Chem.* 4:521–527 (1993)), have been shown to maintain their molecular integrity (150 kDa), and antigen binding capacity.

a. Selective Reduction C2B8/SH:

This method used DTT to partially reduce either the intra or inter molecular disulfide bond and allow IgG/IgG dimers to reform more efficiently. 0.045 mg of Dithiothreitol (DTT Pierce Product #:20290) in calcium and magnesium free PBS, pH 7.4 (cmfPBS,) was added to 21.8 mg of pA purified MAb C2B8/SH in cmfPBS containing 3.5 mM $Na_2$-EDTA, to give a final ratio of 2.0 moles DTT per mole of MAb. The reaction was immediately degassed and incubated under nitrogen for three hours at 37° C. The MAb was purified from unreacted material using Sephadex G-25 column chromatography (PD-10 columns, Pharmacia Fine Chemicals) that was equilibrated with PBS. The MAb containing fraction was collected according to manufacturers instructions in a final volume of 3.0 ml equilibration buffer (PBS). The selectively reduced C2B8/SH was further incubated for two hours at room temperature in air. The reaction was terminated by the addition of 0.1 ml (100 mM) cysteine, and concentrated using an Ultrafuge™ concentrator with a 30,00 MWCO. Protein concentration was determined by absorbance at 280 nm (1 mg/ml=1.7 AU).

b. Characterization C2B8 (-s-s-) Homodimer:

The material was stored at 4° C. until analysis using SDS/PAGE (FIG. 5, lane 4) and analytical HPLC (FIG. 7, Table I). Disulfide linked homodimer, increased from 17.5% in the starting material to 39.4% after selective reduction and dimerization. Repeat synthesis using this method showed dimers ranging from 39.4% of the population to 51% of the starting material.

The 300-kDa disulfide (-s-s-) linked homodimer was purified from monomer and higher molecular weight aggregates using preparative HPLC. Preparative SE-HPLC was performed using a Beckman 126 HPLC system operating isocratically at a flow rate of 4.0 ml/min. with a mobile phase consisting of 100 mM sodium phosphate, 150 mM sodium chloride, pH 6.8. The separation was performed at room temperature using a 21.5×75 mm TosoHaas TSK-Gel SW guard column attached to a 21.5×300 mm TosoHaas TSK-Gel G3000-SW column. Fractions were collected manually by monitoring the computer trace of Absorbence at 280 nm in real time. In general, homodimers were >95% pure after HPLC purification.

EXAMPLE 3

(Ntb #:1966/78): Preparation of C2B8, Thioether Linked, Homodimer (FIG. 4.2)

a. Selective Reduction C2B8:

5.45 mg of pA purified C2B8/SH ($7.27\times10^{-5}$ M) in 0.5 ml cmfPBS/EDTA was reduced with a 2 fold molar excess of DTT for three hours at 37° C. using conditions described in example 2. The selectively reduced MAb was applied to a PD-10 column, equilibrated with deoxygenated normal saline containing sodium citrate (10 mM) and EDTA (1 mM) buffered to pH 6.3 using hydrochloric acid (Saline/Citrate buffer). The first antibody containing peak, in 3.0 ml equilibration buffer (Saline/Citrate buffer), was collected following manufacturer instructions. Protein concentration was determined by absorbance at 280 nm (1 mg/ml=1.7 AU).

The thiol concentration (SH content) estimated using Ellmans reagent was found to average approximately 2 moles of free thiol for each mole DTT-reduced C2B8/SH. Molecular integrity was confirmed with this method using SDS non-reducing PAGE.

b. Homodimer (-s-) Reaction:

Bismaleimidohexane (BMH, Pierce Chemical Co. Product #:22319) was diluted to 10 mM in DMF and added to the selectively reduced C2B8/SH to give a final molar ratio of 2.5 moles BMH per mole MAb. The mixture was rotated for 2.5 hours at room temperature in a $N_2$ atmosphere. The reaction was terminated by the addition of 0.1 ml Cysteine (100 mM in PBS) and stored at 4° C. (normal atmosphere) until analysis and purification using HPLC.

The mixture was analyzed using the analytical HPLC method described in example 2. The fraction (300 kDa) containing the thioether linked (-s-) C2B8 homodimer represented 28% of the total protein collected (FIG. 7 and Table 1). Preparative HPLC (as described in example 2) was used to purify the (-s-) homodimer from the unpurified mixture with purity typically >95%, as determined by SDS-PAGE (non-reducing) gels and analytical HPLC (results not shown). Analysis of the purified C2B8 (-s-) homodimer by SDS/PAGE under reducing conditions showed three major protein bands at approximately MW of 22 kDa (L chain), 55 kDa (H-chain) and 110 kDa (H—H dimer) (FIG. 6, Lane 7). In contrast, disulfide linked homodimer or monomer Ab showed the 2 expected protein bands at 22 and 55 kDa.

EXAMPLE 4

Figure 8:
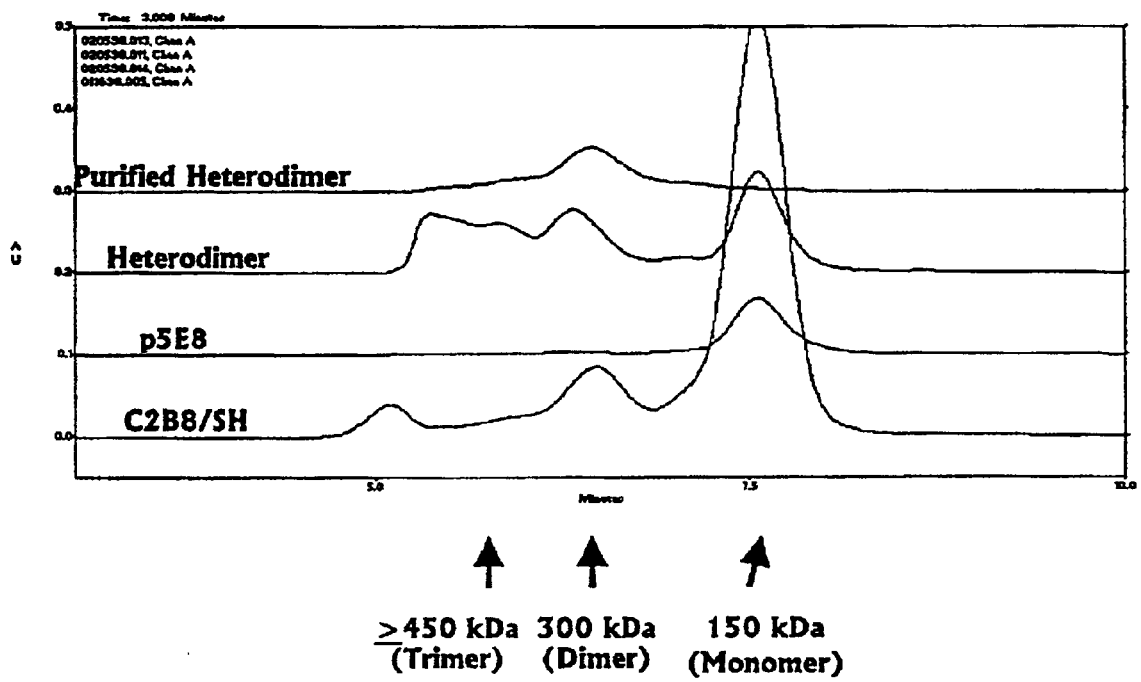
FIG. 8 contains HPLC analysis of C2B8/p5E8 heterodimers (αCD20/αCD23 dimer).

(Ntb #;1266/85): Preparation of C2B8, Thioether Linked, p5E8 Heterodimer (FIG. 4.3)

a. Selective Reduction C2B8:

Purified C2B8/SH, 10.9 mg in 1.0 ml cmfPBS ($7.27\times10^{-5}$M,), was reduced using a 2 fold molar excess of DTT (three hours at 37° C., $N_2$ atm.), using conditions described in example 2, and purified using PD-10 columns equilibrated with Saline/Citrate buffer. The molar ratio of thiol to MAb, determined using Ellmans reagent, as described in example 3, was 1.2. Reduced C2B8/SH was immediately mixed with MAb p5E8 (anti-CD23) that was previously modified with Succinimidyl 4-(p-maleimidophenyl)-butyrate (SMPB, Pierce Chemical Co., Product #22315).

b. SMPB Modified p5E8:

MAb p5E8 ($4.5\times10^{-5}$ M in PBS) was functionalized by addition of a 6 fold molar excess of SMPB (10 mM in DMF), and rotating the mixture for two hours at room temperature. The MAb fraction was purified from unreacted material using PD-10 columns equilibrated with Saline/Citrate buffer. Protein concentration of the SMPB functionalized MAb was determined spectrophotometrically:

$$MAb(mg/ml)=[Absorbence\ 280]\times[dilution\ factor]/1.5$$

c. Heterodimer Formation:

Heterodimer (anti-CD20/anti-CD23) was prepared by mixing 1.5 mole equivalents of SMPB containing p5E8 (11.37 mg) with 1 mole equivalent freshly reduced C2B8/SH (8.0 mg) for one hour at room temperature in a $N_2$ atm. Heterodimer was analyzed and purified using HPLC, as described in example 2. FIG. 8 and Table 2 show HPLC chromatograms of unpurified and purified heterodimer compared to starting material. Purity of the 300 kDa heterodimer was >95%, as determined by analytical HPLC (Table 2) and non-reducing and reducing SDS-PAGE gels FIG. 6. Reducing SDS/PAGE (FIG. 6, lane 6) also showed three major protein bands after reduction, including a non-reducible 110 kDa band, consistent with the formation of thioether linked H—H dimer.

EXAMPLE 5

Binding Activity of C2B8 Homodimer and C2B8/p5E8 Heterodimer

Figure 9:
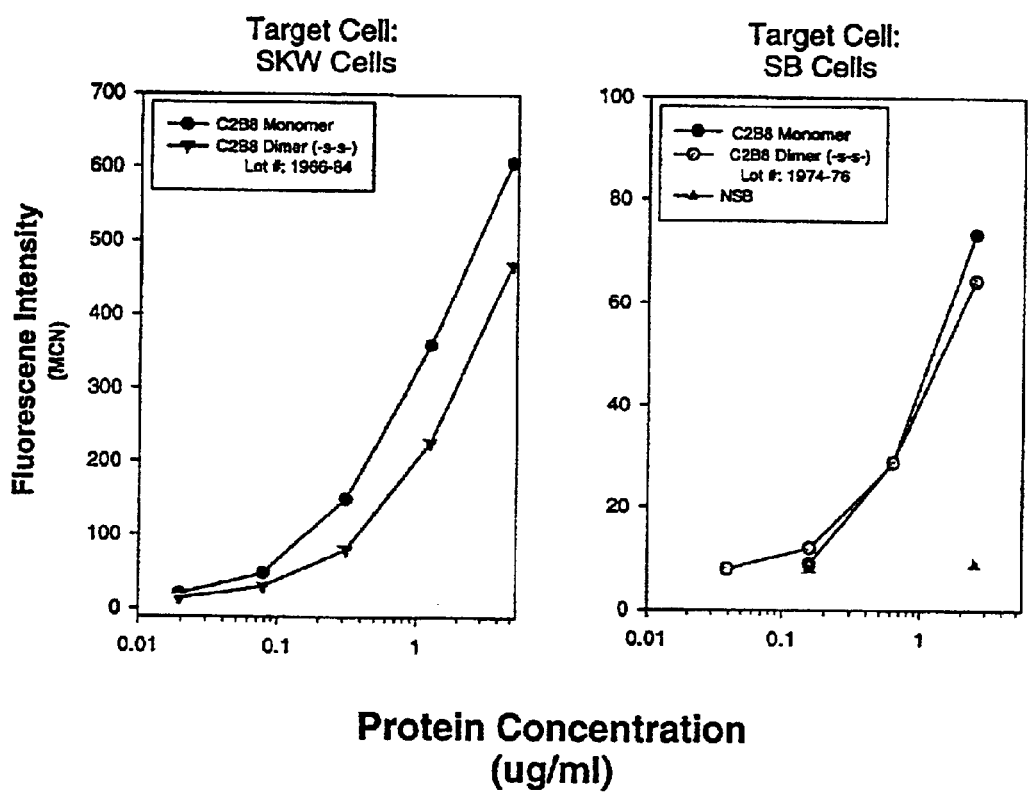
FIG. 9 shows binding of C2B8 (-s-s-) homodimer to CD20 positive cell lines (SKW and SB).

Binding of monomer and dimerized antibody to various cells was evaluated by indirect immunostaining using FITC anti-human IgG and analyzed using flow cytometry (indirect IF). Cells ($2\times10^6$ viable cells in 0.1 ml cmfPB S/2% Fetal Calf Serum/0.1% Sodium Azide, PBS/FCS buffer) were incubated for one hour on ice with 0.1 ml of 5 fold serially diluted antibody. Cells were twice washed by centrifugation (200×g) using 2 ml PBS/wash and suspended in 0.2 ml FITC conjugated Goat (Fab')$_2$ anti-human IgG (Jackson Immunoresearch #30869, 5 µg/ml in PBSIFCS buffer). After 30-min. incubation on ice, cells were again washed in PBS and suspended in 0.2 ml 0.5% freshly diluted formaldehyde, capped and stored at 4° C. until analysis. The amount of cell bound antibody was determined by flow cytometry (FACScan, Becton-Dickenson, Mountain View, Calif.).

a. C2B8 Homodimer:

FIG. 9 compares the binding of MAbs: C2B8 (disulfide linked) homodimer, C2B8, and RF-2 on the CD20+/CD23+ positive cell lines, SKW and SB. RF-2 was used as an isotype matched non-binding antibody control. Similar binding curves for both the C2B8 monomer and dimer was obtained on both cell lines, suggesting similar binding activity for the CD20 antigen.

Figure 10:
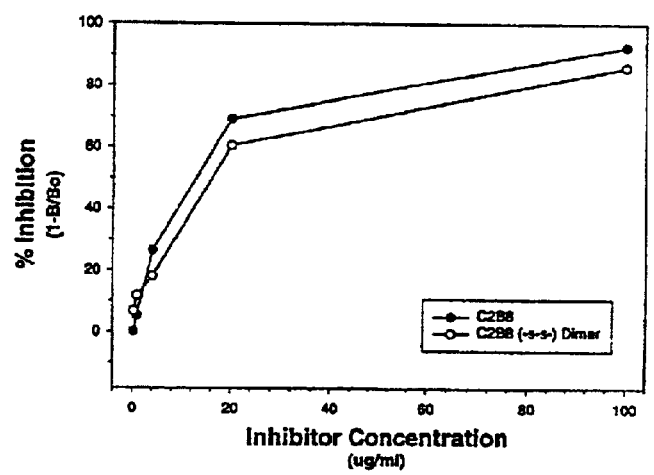
FIG. 10 contains results of a competitive binding assay of C2B8 and C2B8 (-s-s-) homodimer on SKW cells.
Figure 11:
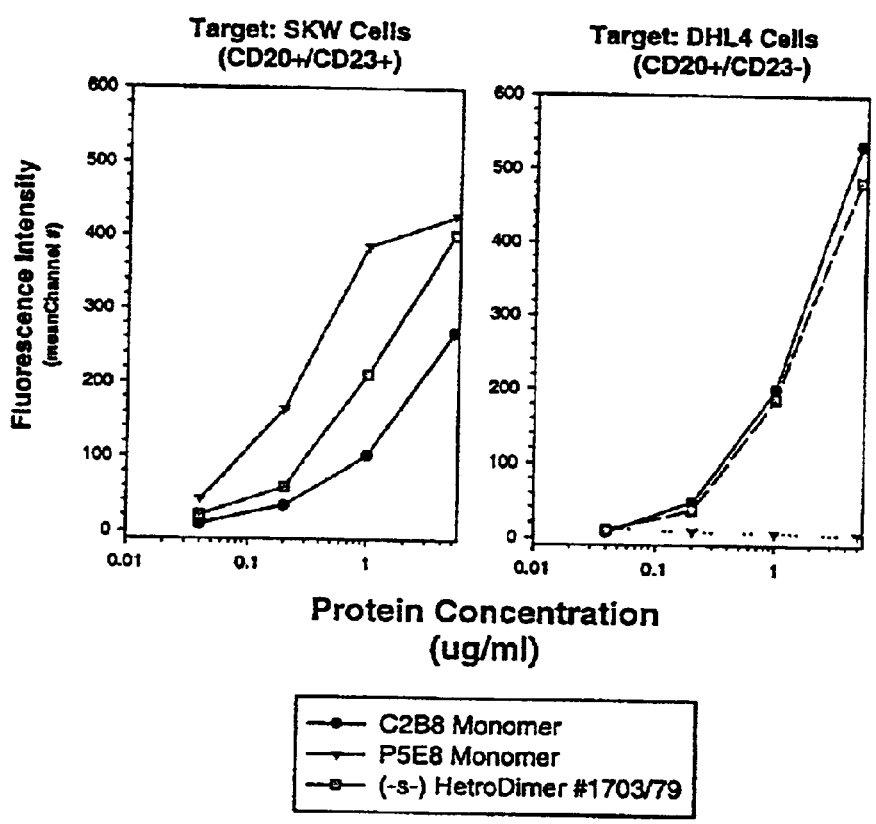
FIG. 11 shows binding of αCD20/αCD23 heterodimer (C2B8/p5E8) to SKW and DHL-4 cell lines.

The binding affinity of the C2B8 homodimer and monomer for the CD20 antigen was compared using a competitive binding assay (FIG. 10). SKW cells were first incubated for 30 minutes on ice with various amounts of 5-fold serially diluted murine (anti-CD20) MAb 2B8, and by 0.1 ml (at 1 µg/ml) of either C2B8 monomer or homodimer. Indirect IF, as described for FIG. 9, evaluated the amount of C2B8 binding. Previous experiments had demonstrated no reactivity of the FITC anti-human IgG for the murine 2B8 antibody. The concentration of C2B8 that gave 50% inhibition of 2B8 antibody binding was 9.8 µg/ml, and 10.4 µg/ml for the homodimer. Data of both FIGS. 9 and 10, therefore, indicate no significant effect on binding affinity for the CD20 antigen as a result of dimerization to a 300 kDa species. Direct staining and FCM analysis, as described in FIG. 9, using thioether linked C2B8 homodimer was similar to results obtained using the disulfide linked dimer (not shown).

b. C2B8/p5E8 Heterodimer:

Binding of C2B8/pSE8 Heterodimer, C2B8 and p5E8 on SKW (CD20+/CD23+) and DHL4 (CD20+/CD23-) cells is shown on FIG. 11. Similar binding curves comparing monomer to heterodimer were obtained on both cell lines, including CD23 antigen negative DHL-4 cells. The data strongly suggested that the heterodimer, like the anti-CD20 homodimers, retained full functional binding for the CD20 antigen.

Figure 12:
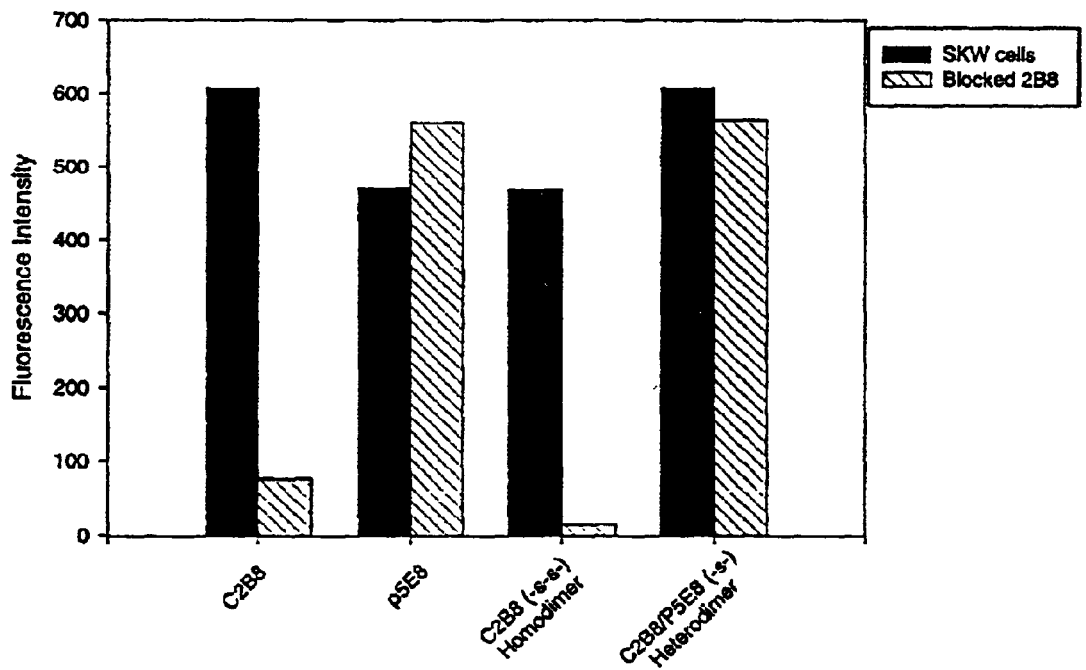
FIG. 12 shows binding of αCD20 C2B8 homodimer and αCD20/αCD23/p5E8 heterodimer to SKW cells (CD20+/CD23+).

To determine heterodimer binding activity for the CD23 antigen, SKW cells ($1\times10^6$ cells PBS/FCS buffer) were first incubated with a saturating amount (10 g/ml) of the murine (anti-CD20) MAb 2B8, followed by binding of either monomer or dimer antibody preparations (FIG. 12). Murine 2B8 completely inhibited binding of both monomer and dimerized C2B8 antibody, but did not effect the binding of either p5E8 or of the Heterodimer. The data suggests that the heterodimer also retained full functional binding activity for the CD23 antigen after dimerization with C2B8.

EXAMPLE 6
Anti-tumor Activity of C2B8 Homodimer in Murine Animal Models

The Daudi human lymphoma tumor line was established in BALB/c nu/nu mice from tissue culture and maintained as a tumor xenograft via sc. inoculation of tumor Brie. Caliper measurements in two perpendicular directions at weekly intervals measured tumor size. Tumor volume was estimated from size measurements by the formula: Tumor Volume ($mm^3$)=Length×(Width)$^2$/2

MAb treatments were administered i.p. on various schedules indicated for each experiment. Antibody was diluted in PBS and administered i.p. as mg per mouse with 8 animals in each group. Control groups remained untreated. Data is reported as median tumor volume for control or treated animal groups. A complete regression was defined as a failure to detect tumor for at least two measurements (>2 weeks).

Figure 13:
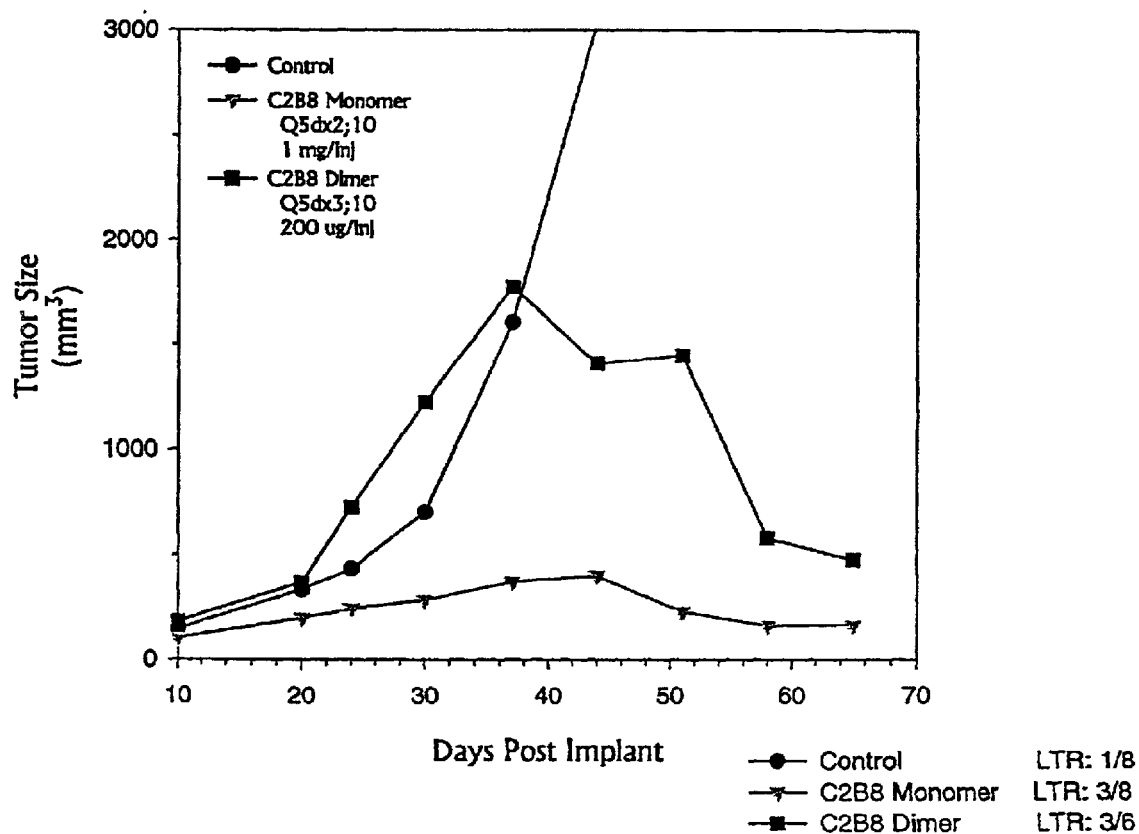
FIG. 13 shows anti-tumor activity of C2B8 chemical (-s-s-) dimers on Daudi tumor xenografts.
Figure 14:
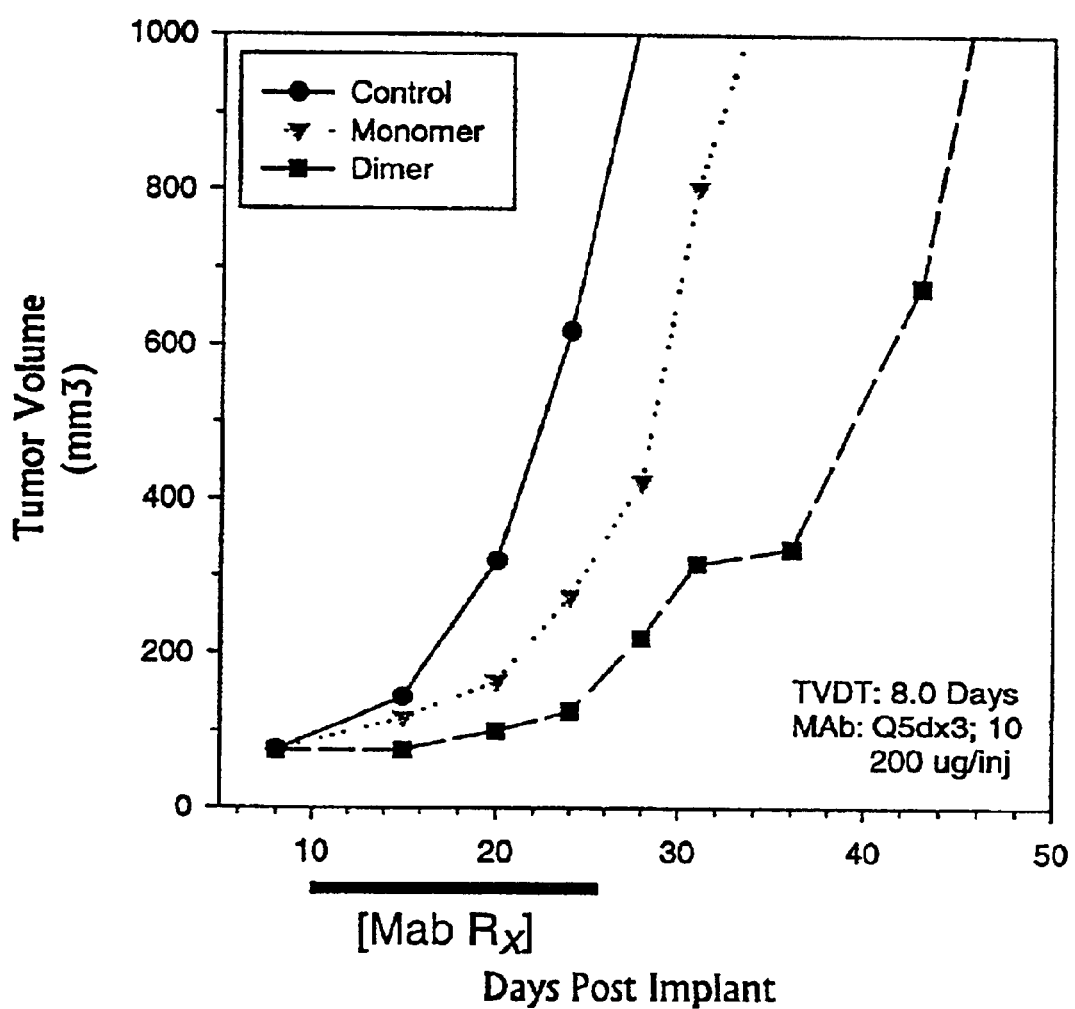
FIG. 14 shows anti-tumor activity of C2B8 (-s-s-) dimers on Daudi tumor xenografts.

The anti-tumor activity of C2B8 tested on established Daudi tumors is shown in FIGS. 13 and 14. FIG. 13 compares anti-tumor activity of low-dose (200 µg/mouse) C2B8 homodimer (schedule: every 5 days×3 injections, Q5dx3) to the activity of dose and schedule optimized C2B8 monomer (1 mg/mouse, Q5dx2).

MAb treatment was initiated on established tumors, 50–150 $mm^3$ at start of treatment At this dose and schedule, the C2B8 homodimer showed tumor growth inhibition comparable to dose optimized C2B8. By day 65, 50% of the animals treated with 200 ug x3 doses of C2B8 homodimer showed complete tumor regression. Animals receiving 1 mg×2 doses of C2B8 had 37.5% complete regressions.

FIG. 14 compares the activity at matching schedules (Q5dx3) of 200 ag/mouse C2B8 monomer or homodimer on established tumors 150–250 $mm^3$ in size. Tumor growth of the C2B8 homodimer treated mice was inhibited to a greater extent than a comparable amount of the C2B8 monomer. At this dose (0.2 mg/mouse), 62.5% of the homodimer treated mice had completely regressed tumors, while 25% of monomer treated mice showed complete tumor regression.

Figure 15:
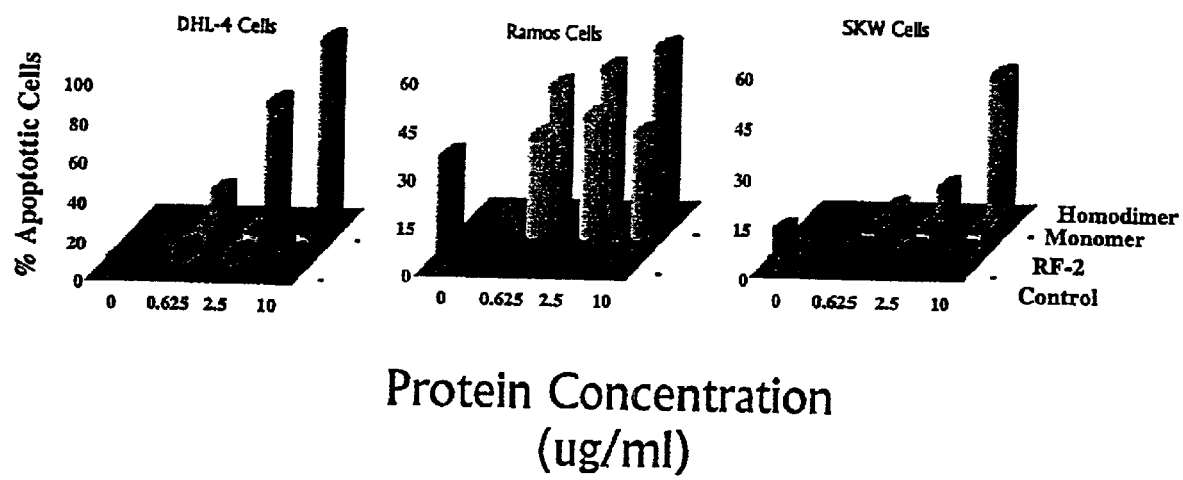
FIG. 15 shows apoptotic activity of C2B8 (-s-s-) homodimer.

EXAMPLE 7
Apoptotic Activity of C2B8 Disulfide Linked Homodimer on B Cell Lymphoma Cells The ability of homodimers to induce apoptosis of CD20 B cell lymphoma cells was determined by TUNEL assay. Disulfide linked homodimer was compared to C2B8 and RF2 on DHL-4 (CD20+), Ramos (CD20+, CD23+) and SKW (CD20, CD23+) cells ($1\times10^6$ cells/ml) at log-phase of growth. The cells were propagated in RPMI 1640 (Irvine Scientific) plus 5% Fetal Bovine Serum (FBS) with 2 mM L-Glutamine (Irvine Scientific) and 100 U/ml of Penicillin-Streptomycin (Irvine Scientific) at 37° C. in 5% $CO_2$) incubator. As controls, cultures were incubated with either C2B8 monomer or a irrelevant isotype matched antibody control, RF2. After 72 hours of incubation, cells were harvested by centrifugation at 350×g for 5 minutes and fixed with 70% (v/v) ethanol (ice-cold) for 30 minutes. Fixed cells were analyzed for apoptosis by a flow cytometry based TUNEL assay using APO-BRDU™ Kit as per manufacturer's instructions (Pharmingen). The treatment of DHL-4 and SKW cells by C2B8 homodimer showed evidence of apoptotic death of cells dependent on the dose of antibody used (FIG. 15 and Table III). In contrast, treatment of cells with same concentrations of C2B8 monomer or the control antibody, RF2 showed no evidence of apoptosis. In addition, with Ramos cells (CD20+Burkitt's lymphoma cell line) that are susceptible to higher degree of spontaneous apoptosis in culture, the addition of homodimers to these culture resulted in enhanced apoptosis (FIG. 15).

EXAMPLE 8

Figure 16:
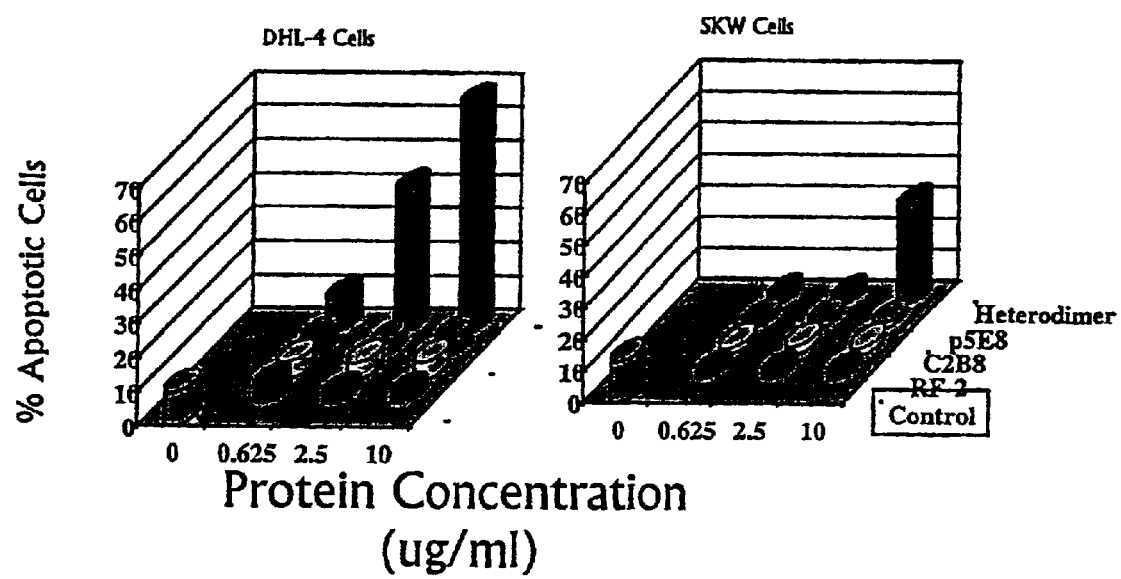
FIG. 16 shows apoptotic activity of C2B8/p5E8 (s) heteromer.

Apoptotic Activity of C2B8-p5E8 Thioether Linked Heterodimer on B Cell Lymphoma Cells The ability of heterodimers to induce apoptosis of CD20+B cell lymphoma cells was determined by TUNEL assay. B lymphoma cells were grown and evaluated, as described in Example 7. Briefly, varying concentrations of heterodimer were added to DHL-4 and SKW cells at log-phase of growth and tested for apoptosis induction as described above in Example 7. As controls, cultures were incubated with C2B8 monomer, p5E8 monomer and an irrelevant antibody control, RF2. FIG. 16 and Table III show the induction of apoptosis in DHL-4 and SKW cells by C2B8 heterodimer in a dose-dependent manner. In cells cultured with C2B8 and p5E8 monomers or the control antibody RF2, no evidence of apoptosis was observed.

EXAMPLE 9

C2B8 Homodimers mediated complement dependent cytotoxicity of normal B cells

The ability of C2B8 homodimers to mediate killing of peripheral blood B cells by complement dependent cytotoxic (CDC) mechanism was demonstrated using a modified flow cytometry based assay. Peripheral blood mononuclear cells (PBMC) were isolated from blood of healthy human donors by Ficoll-Hypaque gradient centrifugation. Viability was determined by Trypan blue dye exclusion and was >98%. Upon isolation, 0.5–1×10$^6$ PBMC's per tube were incubated at room temperature for 45 minutes with either C2B8 (-s-s) homodimer or monomer, and washed with 2 ml of HBSS by centrifuigation and aspiration of supernatant to remove unbound antibodies. The cell pellet was re-suspended with 100 µl rabbit complement (ICN/Cappel Cat. #55866) at different dilutions and incubated for 60 minutes at 37° C. After incubation, 10 µl of anti-CD 19-FITC antibody (Pharmingen) was added. Cells were incubated on ice for 30 minutes, followed by addition of 50 µl (20 µg/ml) of Propidium iodide (PI; Boehringer Mannheim). Fifteen minutes later, 400 µl of HBSS was added to all tubes and the cells were immediately analyzed by FACScan (Becton-Dickinson).

Data was analyzed using the WinList software package, as described by the manufacturer (Variety Software House). Purity of the lymphocyte preparation used for the assay was found to be greater than 95% as determined by the Leucogate (CD45 positive cells). The CDl9+cell (B cell lineage) population of the total lymphocyte population (CD45+) was gated for further analysis. The percentage of CDI 9+cells incorporating PI represented the dead or dying cell population and was determined using the WinList Software. Data in Table I show that the C2B8 homodimer is effective in mediating CDC of peripheral CD19+B cells. Cells incubated with complement alone at 1:10 and 1:20 dilutions (Table IV) had a 20% cytotoxicity which increased to 34% and 41%, respectively, when cells were incubated with C2B8 homodimer (70% increase over control). Control cells incubated without complement showed less than 10% cytotoxicity (data not shown).

TABLE I

Complement-Dependent Cytotoxicity of C2B8 Dimers on CD19+ B Cells

| Antibody[a] | % Cytotoxicity[b] Complement dilution | |
|---|---|---|
| | 1:10 | 1:20 |
| C2B8 dimer | 34.19 | 41.29 |
| C2B8 monomer | 28.89 | 23.86 |
| No antibody control | 20.10 | 20.28 |

[a]Antibody was tested at the optimum concentration of 2 µg/ml, as determined from a previous experiment.
[b]% Cytotoxicity was determined as the percentage of CD19+ cells that showed uptake of propidium iodide stain.

EXAMPLE 10

Growth Inhibition of B Cell Lymphomas by C2B8 Homo and Hetero Dimers

The ability of homodimers and heterodimers to directly inhibit the growth of B lymphoma cell lines SKW and SB was determined by a proliferation inhibition assay. Briefly, varying concentrations of C2B8, p5E8, C2B8 homodimer and C2B8-p5E8 were added to 5×10$^5$ in 96-well flat bottom plates in 20011 of growth medium (5% FBSRPMI-1640 medium) and incubated for 96 hours at 37° C. with 5% $CO_2$. During the last 18 hours of incubation, 50 µl of redox dye alamar blue (Biosource International, Cat. DAL 1100) was added to each well. Following incubation, plates were cooled to room temperature for 10 minutes on a shaker and the intracellular reduction of the dye was determined and fluorescence was read using a 96-well fluorometer with excitation at 530 nm and emission at 590 nm.

The results are expressed as relative fluorescence units (RFU). The percentage growth inhibition was calculated as: [1−(Average RFU of Test sample ÷Average RFU of no antibody control)]×100%. As indicated in the FIG. 17, C2B8 homodimer and the beterodimers showed inhibition of both SKW and SB cell growth in vitro in a dose-dependent manner. Consistent with our previous findings, the C2B8 and p5E8 monomers did not inhibit growth of SKW and SB cells. In contrast, both C2B8 (-s-s-) and C2B8-p5E8 (-s) showed dose dependent inhibition of cell growth. IC50 values for homodimer were 0.625 µg/ml for SKW and for SB cells, while IC 50 values for the heterodimers raised from 0.625 µg/ml to 1.41 µg/ml.

EXAMPLE 11

Growth Inhibition of B Cell Lymphoma by Cross-linking of C2B8 Monomers

The ability to enhance the biological activity by hyper cross-linking of membrane CD20 was first demonstrated using B cell lymphoma cell lines in a proliferation inhibition assay. Briefly, 3×10$^4$ DHL-4 or SB cells in RPMI-1640 growth medium containing 10% FCS was added to each well of 96-well U-bottom plate and incubated with increasing concentrations of C2B8. After 1 hour of incubation at 37° C., 50 µl of murine monoclonal anti-human IgGI antibody (Sigma Chemical Co.) at 10 µg/ml of final concentration was added to each well and incubated for an additional 72 hours. During the last 18 hours incubation, cultures were pulsed with 1 µCi per well of [$^3$H]-thymidine. Cells were washed, harvested and cell-associated radioactivity measured using an automated liquid scintillation counter.

A representation of the data from the cell proliferation experiment is shown in FIG. 18, which indicates that hyper cross-linking of C2B8 on the surface of B cell lymphoma using a secondary antibody showed a clear dose dependent inhibition of cell proliferation, which was not observed when CD20+B cells were incubated with monomeric C2B8.

Antibodies tested under similar conditions on CD20 HSB cells showed no effect, indicating that the observed effect was mediated via the CD20 molecule on the surface of B cell lymphomas. In addition, cross-linking of C2B8 by direct coating of culture wells without a secondary antibody prior to the addition of cells also resulted in inhibition of cell growth, further confirming above observation (data not shown).

EXAMPLE 12

Apoptotic Activity of C2B8 Disulfide Linked Homodimer on PBMC Isolated from a CLL Patient The ability of C2B8 homodimer to induce apoptosis using CD20+B cells from human patients diagnosed with chronic lymphocytic leukemia (CLL) was also determined by TUNEL assay. Disulfide linked homodimer was compared to monomer for apoptosis induction on lymphocytes isolated from a donor diagnosed with CLL. The PBMC were cultured in RPMI 1640 medium supplemented with 2% donor plasma, plus 2 mM L-Glutamine and 100 U/ml of Penicillin-Streptomycin. As controls, cultures were incubated with C2B8 monomer and the non-binding MAb RF2. After 120 hours of incubation, cells were harvested and fixed with 70% (v/v) ethanol and analyzed for apoptosis by TUNEL assay, as descried earlier (Example 7). The treatment of leukemic cells by C2B8 homodimer resulted in approximately 20% increased cell death by apoptosis, compared to cells that were with the same concentrations of C2B8 monomer or the control antibody, RF2 (Table II). Overall, a high level of spontaneous apoptotic cell death was observed with CLL-B cell, which may be the result of the suboptimal culture conditions used in these studies.

TABLE II

Induction of Apoptosis by C2B8 Homodimer of CD 19$^+$/CD20$^+$ B Cells from a CLL Patient

| Clinical Sample | Treatment | Apoptosis[a] | | |
|---|---|---|---|---|
| | | 10 μg/ml | 2.5 μg/ml | 0.625 μg/ml |
| CSK#1 | C2B8-C2B8 | 84% | 83% | 65% |
| | C2B8 | 64% | 65% | 63% |
| | RF2 | 62% | 67% | 60% |

[a]Apoptosis was determined by Tunel assay, as described under example 7. Degree of apoptosis was expressed as % apoptosis by sample divided by % apoptosis of controls. Flow cytometric analysis was performed on Becton-Dickinson FACScan using a FACScan Research Software package and the final data analysis was performed using the WinList Software package (Variety Software House). Percentage of cells positive for apoptosis was determined as the percentage of gated cells that were positive above the background, autofluorescence.

What is claimed is:

1. A method for producing an antibody heterodimer comprising an anti-CD20 antibody and an anti-CD23 antibody, comprising:
   (i) obtaining or constructing a DNA molecule that encodes an antibody molecule heavy chain that has binding specificity to a CD20 or CD23 antigen when said heavy chain is paired with a corresponding light chain, and introducing at least one cysteine codon into said antibody molecule heavy chain via recombinant DNA mutagenesis;
   (ii) expressing said DNA molecule in a suitable host cell, or expression system, together with a DNA molecule that encodes an antibody molecule light chain having the same specificity as the heavy chain, to produce a first anti-CD20 or anti-CD23 antibody molecule containing said introduced cysteine residue;
   (iii) purifying said first antibody molecule from said host cell or expression system;
   (iv) contacting said purified antibody molecule with an amount of a suitable reducing agent sufficient to partially reduce the intra or inter molecular disulfide bonds of said antibody molecule and thereby enhance dimerization of said first antibody molecule with a second antibody molecule; and
   (v) contacting said purified first antibody molecule with a second antibody molecule that has a binding specificity to CD20 when said first antibody is an anti-CD23 antibody, or to CD23 when said first antibody is an anti-CD20 antibody, and allowing sufficient time for dimerization to proceed to thereby to produce a tetravalent antibody heterodimer comprising both an anti-CD20 antibody and an anti-CD23 antibody, wherein following dimerization, the anti-CD20 antibody of the heterodimer has binding specificity to CD20 and the anti-CD23 antibody of the heterodimer has binding specificity to CD23.

2. A method according to claim 1, wherein said first and second antibodies are both IgG antibodies.

3. A method according to claim 2, wherein said first and second antibodies are both IgG-1 antibodies.

4. A method according to claim 1, wherein the anti-CD20 antibody has binding specificity to a human CD20 antigen and the anti-CD23 antibody has binding specificity to a human CD23 antigen.

5. A method according to claim 4, wherein the anti-human CD20 antibody is a chimeric antibody consisting of light and heavy chains of a human IgG antibody in which the variable regions are replaced with the light and heavy chain variable regions of murine C2B8 antibody, and
   the anti-human CD23 antibody is a chimeric antibody consisting of light and heavy chains of a human IgG antibody in which the variable regions are replaced with the light and heavy chain variable regions of monkey 5E8 antibody.

6. A method according to claim 5, wherein said first and second antibodies are both IgG-1 antibodies.

7. A method according to claim 1, wherein the location of said cysteine molecule is such that it prevents or inhibits formation of an intramolecular disulfide bridge between sister heavy chains on the same antibody molecule.

8. A method according to claim 1, wherein step (iv) further comprises terminating the reducing reaction by the addition of cysteine blocking reagent.

9. A method according to claim 1, wherein step (v) comprises cross-linking the reduced antibody molecules using a BIS-maleimido cross-linker.

10. A method according to claim 1, wherein the second antibody contains a thiol reactive group other than a cysteine group introduced therein.

11. The method of claim 10, wherein the thiol reactive group is selected from the group consisting of a maleimido group, a dithiopyridal group, and a reactive thiol.

12. A method of claim 10, wherein step (iv) further comprises terminating the reducing reaction by the addition of thiol blocking reagent.

13. A tetravalent antibody heterodimer produced by the method of claim 1.

14. An antibody heterodimer according to claim 13, wherein said first and second antibodies are both IgG antibodies.

15. An antibody heterodimer according to claim 14, wherein said first and second antibodies are both IgG-1 antibodies.

16. An antibody heterodimer produced by the method of claim 5.

17. An antibody heterodimer according to claim 16, wherein said first and second antibodies are both IgG-1 antibodies.

18. A tetravalent antibody heterodimer comprising a first antibody that has binding specificity to a CD20 antigen and a second antibody that has binding specificity to a CD23 antigen.

19. The antibody heterodimer of claim 18, wherein said first or said second antibody comprises an antibody heavy chain polypeptide that is mutated by introduction of a cysteine residue.

20. The antibody heterodimer of claim 18, wherein said first and second antibodies are both IgG antibodies.

21. The antibody heterodimer of claim 20, wherein said first and second antibodies are both IgG-1 antibodies.

22. The antibody heterodimer of claim 18, wherein said first and second antibodies are monoclonal antibodies.

23. The antibody heterodimer of claim 18, wherein the anti-CD20 antibody has binding specificity to a human CD20 antigen and the anti-CD23 antibody has binding specificity to a human CD23 antigen.

24. The antibody heterodimer of claim 23,
   wherein the anti-human CD20 antibody is a chimeric antibody consisting of light and heavy chains of a human IgG antibody in which the variable regions are replaced with the light and heavy chain variable regions of murine C2B8 antibody, and
   the anti-human CD23 antibody is a chimeric antibody consisting of light and heavy chains of a human IgG antibody in which the variable regions are replaced with the light and heavy chain variable regions of monkey 5E8 antibody.

25. The antibody heterodimer of claim 24, wherein said first and second antibodies are both IgG-1 antibodies.

26. The antibody heterodimer of claim 24, wherein said first and second antibodies are monoclonal antibodies.

27. The antibody heterodimer of claim 24, which activates components of the complement system.

28. The antibody heterodimer of claim 24, which promotes killing of cells by the complement cascade.

29. The antibody heterodimer of claim 24, which binds to Fcγ receptors on cytotoxic effector cells.

30. The antibody heterodimer of claim 24, which binds to Fcγ receptors on host immune cells.

31. The antibody heterodimer of claim 24, which induces B lymphoma cells to initiate apoptosis.

32. The antibody heterodimer of claim 24, which induces initiation of apoptosis of leukemic cells of a patient with chronic lymphocytic leukemia.

* * * * *

SEQUENCE LISTING

<160> NUMBER OF SEQ ID NOS: 4

<210> SEQ ID NO 1
<211> LENGTH: 708
<212> TYPE: DNA
<213> ORGANISM: Artificial Sequence
<220> FEATURE:
<223> OTHER INFORMATION: Description of Artificial Sequence: DNA
      encoding "Dimeric" Anti-CD20 Light Chain (Version 1)
<221> NAME/KEY: CDS
<222> LOCATION: (1)..(705)

<400> SEQUENCE: 1

```
atg gat ttt cag gtg cag att atc agc ttc ctg cta atc agt gct tca        48
Met Asp Phe Gln Val Gln Ile Ile Ser Phe Leu Leu Ile Ser Ala Ser
 1               5                  10                  15 gtc ata atg tcc aga gga caa att gtt ctc tcc cag tct cca gca atc        96
Val Ile Met Ser Arg Gly Gln Ile Val Leu Ser Gln Ser Pro Ala Ile
             20                  25                  30 ctg tct gca tct cca ggg gag aag gtc aca atg act tgc agg gcc agc       144
Leu Ser Ala Ser Pro Gly Glu Lys Val Thr Met Thr Cys Arg Ala Ser
         35                  40                  45 tca agt gta agt tac atc cac tgg ttc cag cag aag cca gga tcc tcc       192
Ser Ser Val Ser Tyr Ile His Trp Phe Gln Gln Lys Pro Gly Ser Ser
     50                  55                  60 ccc aaa cgc tgg att tat gcc aca tcc aac ctg gct tct gga gtc cct       240
Pro Lys Arg Trp Ile Tyr Ala Thr Ser Asn Leu Ala Ser Gly Val Pro
 65                  70                  75                  80 gtt cgc ttc agt ggc agt ggg tct ggg act tct tac tct ctc aca atc       288
Val Arg Phe Ser Gly Ser Gly Ser Gly Thr Ser Tyr Ser Leu Thr Ile
                 85                  90                  95 agc aga gtg gag gct gaa gat gct gcc act tat tac tgc cag cag tgg       336
Ser Arg Val Glu Ala Glu Asp Ala Ala Thr Tyr Tyr Cys Gln Gln Trp
```

```
                100                 105                 110
act agt aac cca ccc acg ttc gga ggg ggg gcc aag ctg gaa atc aaa      384
Thr Ser Asn Pro Pro Thr Phe Gly Gly Gly Ala Lys Leu Glu Ile Lys
            115                 120                 125 cgt acg gtg gct gca cca tct gtc ttc atc ttc ccg cca tct gat gag      432
Arg Thr Val Ala Ala Pro Ser Val Phe Ile Phe Pro Pro Ser Asp Glu
130                 135                 140 cag ttg aaa tct gga act gcc tct gtt gtg tgc ctg ctg aat aac ttc      480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa      528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc      576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag      624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg      672
Lys His Lys Val Tyr Ala Cys Glu Val Thr His Gln Gly Leu Ser Ser
    210                 215                 220 ccc gtc aca aag agc ttc aac agg gga gag tgt tga                      708
Pro Val Thr Lys Ser Phe Asn Arg Gly Glu Cys
225                 230                 235

<210> SEQ ID NO 2
<211> LENGTH: 235
<212> TYPE: PRT
<213> ORGANISM: Artificial Sequence
<220> FEATURE:
<223> OTHER INFORMATION: Description of Artificial Sequence:
      "Dimeric" Anti-CD20 Light Chain (Version 1)

<400> SEQUENCE: 2

Met Asp Phe Gln Val Gln Ile Ile Ser Phe Leu Leu Ile Ser Ala Ser
 1               5                  10                  15

Val Ile Met Ser Arg Gly Gln Ile Val Leu Ser Gln Ser Pro Ala Ile
             20                  25                  30

Leu Ser Ala Ser Pro Gly Glu Lys Val Thr Met Thr Cys Arg Ala Ser
         35                  40                  45

Ser Ser Val Ser Tyr Ile His Trp Phe Gln Gln Lys Pro Gly Ser Ser
     50                  55                  60

Pro Lys Arg Trp Ile Tyr Ala Thr Ser Asn Leu Ala Ser Gly Val Pro
 65                  70                  75                  80

Val Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Ala Lys Leu Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
```

```
            180                 185                 190
Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235

<210> SEQ ID NO 3
<211> LENGTH: 1413
<212> TYPE: DNA
<213> ORGANISM: Artificial Sequence
<220> FEATURE:
<223> OTHER INFORMATION: Description of Artificial Sequence: DNA
      encoding "Dimeric" Anti-CD20 Heavy Chain (Version 1)
<221> NAME/KEY: CDS
<222> LOCATION: (1)..(1410)

<400> SEQUENCE: 3
```

| | | | | | | | | | | | | | | | | |
|---|---|---|---|---|---|---|---|---|---|---|---|---|---|---|---|---|
| atg | ggt | tgg | agc | ctc | atc | ttg | ctc | ttc | ctt | gtc | gct | gtt | gct | acg | cgt | 48 |
| Met | Gly | Trp | Ser | Leu | Ile | Leu | Leu | Phe | Leu | Val | Ala | Val | Ala | Thr | Arg | |
| 1 | | | | 5 | | | | | 10 | | | | | 15 | | |
| gtc | ctg | tcc | cag | gta | caa | ctg | cag | cag | cct | ggg | gct | gag | ctg | gtg | aag | 96 |
| Val | Leu | Ser | Gln | Val | Gln | Leu | Gln | Gln | Pro | Gly | Ala | Glu | Leu | Val | Lys | |
| | | | 20 | | | | | 25 | | | | | 30 | | | |
| cct | ggg | gcc | tca | gtg | aag | atg | tcc | tgc | aag | gct | tct | ggc | tac | aca | ttt | 144 |
| Pro | Gly | Ala | Ser | Val | Lys | Met | Ser | Cys | Lys | Ala | Ser | Gly | Tyr | Thr | Phe | |
| | 35 | | | | | 40 | | | | | 45 | | | | | |
| acc | agt | tac | aat | atg | cac | tgg | gta | aaa | cag | aca | cct | ggt | cgg | ggc | ctg | 192 |
| Thr | Ser | Tyr | Asn | Met | His | Trp | Val | Lys | Gln | Thr | Pro | Gly | Arg | Gly | Leu | |
| | 50 | | | | | 55 | | | | | 60 | | | | | |
| gaa | tgg | att | gga | gct | att | tat | ccc | gga | aat | ggt | gat | act | tcc | tac | aat | 240 |
| Glu | Trp | Ile | Gly | Ala | Ile | Tyr | Pro | Gly | Asn | Gly | Asp | Thr | Ser | Tyr | Asn | |
| 65 | | | | | 70 | | | | | 75 | | | | | 80 | |
| cag | aag | ttc | aaa | ggc | aag | gcc | aca | ttg | act | gca | gac | aaa | tcc | tcc | agc | 288 |
| Gln | Lys | Phe | Lys | Gly | Lys | Ala | Thr | Leu | Thr | Ala | Asp | Lys | Ser | Ser | Ser | |
| | | | | 85 | | | | | 90 | | | | | 95 | | |
| aca | gcc | tac | atg | cag | ctc | agc | agc | ctg | aca | tct | gag | gac | tct | gcg | gtc | 336 |
| Thr | Ala | Tyr | Met | Gln | Leu | Ser | Ser | Leu | Thr | Ser | Glu | Asp | Ser | Ala | Val | |
| | | | 100 | | | | | 105 | | | | | 110 | | | |
| tat | tac | tgt | gca | aga | tcg | act | tac | tac | ggc | ggt | gac | tgg | tac | ttc | aat | 384 |
| Tyr | Tyr | Cys | Ala | Arg | Ser | Thr | Tyr | Tyr | Gly | Gly | Asp | Trp | Tyr | Phe | Asn | |
| | | 115 | | | | | 120 | | | | | 125 | | | | |
| gtc | tgg | ggc | gca | ggg | acc | acg | gtc | acc | gtc | tct | gca | gct | agc | acc | aag | 432 |
| Val | Trp | Gly | Ala | Gly | Thr | Thr | Val | Thr | Val | Ser | Ala | Ala | Ser | Thr | Lys | |
| | 130 | | | | | 135 | | | | | 140 | | | | | |
| ggc | cca | tcg | gtc | ttc | ccc | ctg | gca | ccc | tcc | tcc | aag | agc | acc | tct | ggg | 480 |
| Gly | Pro | Ser | Val | Phe | Pro | Leu | Ala | Pro | Ser | Ser | Lys | Ser | Thr | Ser | Gly | |
| 145 | | | | | 150 | | | | | 155 | | | | | 160 | |
| ggc | aca | gcg | gcc | ctg | ggc | tgc | ctg | gtc | aag | gac | tac | ttc | ccc | gaa | ccg | 528 |
| Gly | Thr | Ala | Ala | Leu | Gly | Cys | Leu | Val | Lys | Asp | Tyr | Phe | Pro | Glu | Pro | |
| | | | | 165 | | | | | 170 | | | | | 175 | | |
| gtg | acg | gtg | tcg | tgg | aac | tca | ggc | gcc | ctg | acc | agc | ggc | gtg | cac | acc | 576 |
| Val | Thr | Val | Ser | Trp | Asn | Ser | Gly | Ala | Leu | Thr | Ser | Gly | Val | His | Thr | |
| | | | 180 | | | | | 185 | | | | | 190 | | | |
| ttc | ccg | gct | gtc | cta | cag | tcc | tca | gga | ctc | tac | tcc | ctc | agc | agc | gtg | 624 |
| Phe | Pro | Ala | Val | Leu | Gln | Ser | Ser | Gly | Leu | Tyr | Ser | Leu | Ser | Ser | Val | |
| | | 195 | | | | | 200 | | | | | 205 | | | | |
| gtg | acc | gtg | ccc | tcc | agc | agc | ttg | ggc | acc | cag | acc | tac | atc | tgc | aac | 672 |
| Val | Thr | Val | Pro | Ser | Ser | Ser | Leu | Gly | Thr | Gln | Thr | Tyr | Ile | Cys | Asn | |
| | 210 | | | | | 215 | | | | | 220 | | | | | |

```
gtg aat cac aag ccc agc aac acc aag gtg gac aag aaa gtt gag ccc      720
Val Asn His Lys Pro Ser Asn Thr Lys Val Asp Lys Lys Val Glu Pro
225                 230                 235                 240 aaa tct tgt gac aaa act cac aca tgc cca ccg tgc cca gca cct gaa      768
Lys Ser Cys Asp Lys Thr His Thr Cys Pro Pro Cys Pro Ala Pro Glu
                245                 250                 255 ctc ctg ggg gga ccg tca gtc ttc ctc ttc ccc cca aaa ccc aag gac      816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
290                 295                 300 gtg gag gtg cat aat gcc aag aca aag ccg cgg gag gag cag tac aac      960
Val Glu Val His Asn Ala Lys Thr Lys Pro Arg Glu Glu Gln Tyr Asn
305                 310                 315                 320 agc acg tac cgt gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggg cag ccc cga gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gat gag ctg acc aag aac     1152
Pro Gln Val Tyr Thr Leu Pro Pro Ser Arg Asp Glu Leu Thr Lys Asn
370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggg cag ccg gag aac aac tac aag acc     1248
Ala Val Glu Trp Glu Ser Asn Gly Gln Pro Glu Asn Asn Tyr Lys Thr
                405                 410                 415 acg cct ccc gtg ctg gac tcc gac ggc tcc ttc ttc ctc tac agc aag     1296
Thr Pro Pro Val Leu Asp Ser Asp Gly Ser Phe Phe Leu Tyr Ser Lys
            420                 425                 430 ctc acc gtg gac aag agc agg tgg cag cag ggg aac gtc ttc tca tgc     1344
Leu Thr Val Asp Lys Ser Arg Trp Gln Gln Gly Asn Val Phe Ser Cys
        435                 440                 445 tcc gtg atg cat gag gct ctg cac aac cac tac acg cag aag agc ctc     1392
Ser Val Met His Glu Ala Leu His Asn His Tyr Thr Gln Lys Ser Leu
450                 455                 460 tcc ctg tgt ccg ggt aaa tga                                         1413
Ser Leu Cys Pro Gly Lys
465                 470

<210> SEQ ID NO 4
<211> LENGTH: 470
<212> TYPE: PRT
<213> ORGANISM: Artificial Sequence
<220> FEATURE:
<223> OTHER INFORMATION: Description of Artificial Sequence:
      "Dimeric" Anti-CD20 Heavy Chain (Version 1)

<400> SEQUENCE: 4

Met Gly Trp Ser Leu Ile Leu Leu Phe Leu Val Ala Val Ala Thr Arg
1               5                   10                  15
```

```
Val Leu Ser Gln Val Gln Leu Gln Gln Pro Gly Ala Glu Leu Val Lys
            20                  25                  30
Pro Gly Ala Ser Val Lys Met Ser Cys Lys Ala Ser Gly Tyr Thr Phe
        35                  40                  45
Thr Ser Tyr Asn Met His Trp Val Lys Gln Thr Pro Gly Arg Gly Leu
    50                  55                  60
Glu Trp Ile Gly Ala Ile Tyr Pro Gly Asn Gly Asp Thr Ser Tyr Asn
65                  70                  75                  80
Gln Lys Phe Lys Gly Lys Ala Thr Leu Thr Ala Asp Lys Ser Ser Ser
                85                  90                  95
Thr Ala Tyr Met Gln Leu Ser Ser Leu Thr Ser Glu Asp Ser Ala Val
            100                 105                 110
Tyr Tyr Cys Ala Arg Ser Thr Tyr Tyr Gly Gly Asp Trp Tyr Phe Asn
        115                 120                 125
Val Trp Gly Ala Gly Thr Thr Val Thr Val Ser Ala Ala Ser Thr Lys
    130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
        195                 200                 205
Val Thr Val Pro Ser Ser Ser Leu Gly Thr Gln Thr Tyr Ile Cys Asn
    210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
        275                 280                 285
Val Ser His Glu Asp Pro Glu Val Lys Phe Asn Trp Tyr Val Asp Gly
    290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
        355                 360                 365
Pro Gln Val Tyr Thr Leu Pro Pro Ser Arg Asp Glu Leu Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
```

```
                435                 440                 445
Ser Val Met His Glu Ala Leu His Asn His Tyr Thr Gln Lys Ser Leu
    450                 455                 460

Ser Leu Cys Pro Gly Lys
465                 470
```